(12) United States Patent
Acey et al.

(10) Patent No.: US 9,757,399 B2
(45) Date of Patent: Sep. 12, 2017

(54) BUTYRYLCHOLINESTERASE INHIBITORS

(71) Applicant: JAL Therapeutics, LLC, Irvine, CA (US)

(72) Inventors: Roger A. Acey, Long Beach, CA (US); Kensaku Nakayama, Tustin, CA (US)

(73) Assignee: JAL THERAPEUTICS, INC., Long Beach, CA (US)

( * ) Notice: Subject to any disclaimer, the term of this patent is extended or adjusted under 35 U.S.C. 154(b) by 0 days.

(21) Appl. No.: 15/004,797

(22) Filed: Jan. 22, 2016

(65) Prior Publication Data

US 2016/0206635 A1 Jul. 21, 2016

Related U.S. Application Data

(63) Continuation-in-part of application No. 14/071,817, filed on Nov. 5, 2013, now abandoned, which is a continuation-in-part of application No. 12/447,862, filed on Apr. 29, 2009, now abandoned, application No. 15/004,797, which is a continuation-in-part of application No. 12/447,862, filed as application No. PCT/US2007/083262 on Oct. 31, 2007, now abandoned.

(60) Provisional application No. 60/863,764, filed on Oct. 31, 2006.

(51) Int. Cl.
| | |
|---|---|
| *A61K 31/661* | (2006.01) |
| *A61K 31/6615* | (2006.01) |
| *A61K 9/00* | (2006.01) |
| *C07F 9/12* | (2006.01) |
| *C07F 9/18* | (2006.01) |
| *C07F 9/24* | (2006.01) |

(52) U.S. Cl.
CPC ........ *A61K 31/6615* (2013.01); *A61K 9/0019* (2013.01); *C07F 9/12* (2013.01); *C07F 9/18* (2013.01); *C07F 9/242* (2013.01)

(58) Field of Classification Search
None
See application file for complete search history.

(56) References Cited

U.S. PATENT DOCUMENTS

| | | | |
|---|---|---|---|
| 2,944,937 | A | 7/1960 | Moyle et al. |
| 6,683,105 | B2 | 1/2004 | Greig et al. |
| 2010/0069337 | A1 | 3/2010 | Acey et al. |
| 2014/0073608 | A1 | 3/2014 | Acey et al. |
| 2016/0206635 | A1 | 7/2016 | Acey et al. |

FOREIGN PATENT DOCUMENTS

| | | |
|---|---|---|
| CA | 2257161 | 1/1998 |
| CA | 2276356 | 7/1998 |
| CA | 2318817 | 8/1999 |
| CA | 2372500 | 11/2000 |
| CA | 2402224 | 9/2001 |
| WO | 9800021 | 1/1998 |
| WO | 9829424 | 7/1998 |
| WO | 9938873 | 8/1999 |
| WO | 9952516 | 10/1999 |
| WO | 9958555 | 11/1999 |
| WO | 0064912 | 11/2000 |
| WO | 0166552 | 9/2001 |

OTHER PUBLICATIONS

Nakayama et al., Differential inhibition of acetylcholinesterase and butyrylcholinesterase by phosphotriesters, Abstracts of Papers, 227th American Chemical Society.*
Greig et al., Selective butyrylcholinesterase inhibition elevates brain acetylcholine, augments learning and lowers Alzheimer β-amyloid peptide in rodent, PNAS, Nov. 22, 2005, vol. 102 No. 47, pp. 17213-17218.*
Law et al., "Differential inhibition of acetylcholinesterase and butyrylcholinesterase by dialkyl phenyl phosphates", FASEB journal, May 14, 2004, 18(8), Suppl. S, pp. C140-C141.*
Law et al., Differential inhibition of acetylcholinesterase and butyrylcholinesterase by phosphotriesters, Abstracts, 38th Western Regional Meeting of the American Chemical Society, Long Beach, CA, United States, Oct. 15-18, 2003, Publisher: American Chemical Society, Washington D.C.*
Law et al., Differential inhibition of acetylcholinesterase and butyrylcholinesterase by phosphotriesters, Abstracts, 38th Western Regional Meeting of the American Chemical Society, Long Beach, CA, United States, Oct. 15-18, 2003.*
Batra et al., "Phase transfer catalysed phosphorylation of phenols: Phosphate esters," Indian Journal of Chemistry—Section B Organic Chemistry Including Medicinal Chemistry, vol. 30, No. 1, 1991, pp. 57-58.
Budnikova et al., "Dimer formation in the reaction of aryl halides catalysed by nickel complexes," Bulletin of the Russian Academy of Sciences, Division of Chemical Science, vol. 41, No. 7, 1992, pp. 1299-1300.
Burger, "Isosterism and bioisosterism in drug design," Progress in Drug Research, vol. 37, 1991, pp. 287-328.
De Roos et al., "The preparation of some dialkyl p-nitrophenyl phosphates," Recueil Des Travaux Chimiques Des Pays-Bas, vol. 77, 1958, pp. 946-950.
Eddleston et al., "Differences between organophosphorous insecticides in human self-poisoning: a prospective cohort study," The Lancet, vol. 366, 2005, pp. 1452-1459.
Eddleston et al., "Management of acute organophosphorus pesticide poisoning," The Lancet, vol. 371, 2008, pp. 597-607.
Grifman et al., "In vitro phosphorylation of acetylcholinesterase at non-consensus protein kinase A sites enhances the rate of acetylcholine hydrolysis," Molecular Brain Research, vol. 51, 1997, pp. 179-187.

(Continued)

*Primary Examiner* — Svetlana M Ivanova
(74) *Attorney, Agent, or Firm* — K&L Gates LLP; Louis C. Cullman

(57) ABSTRACT

Butyrylcholinesterase inhibitors, their formulation, and their use primarily in the treatment of neurodegenerative diseases. These inhibitors generally are phosphates, phosphonates, phosphinates, and phosphoramidates.
These inhibitors can be incorporated in pharmaceutical compositions and administered to a patient in therapeutically effective amounts to treat neurodegenerative diseases.

19 Claims, 10 Drawing Sheets

(56) References Cited

OTHER PUBLICATIONS

Greig et al., "Selective butyrylcholinesterase inhibition elevates brain acetylcholine, augments learning and lowers Alzheimer β-amyloid peptide in rodent," PNAS, 2005, vol. 102, No. 47, pp. 17213-17218.
Jentzsch et al., "Organophosphorverbindungen. VI. Quantitative Untersuchungen uber das Alkylierungsvermogen kernsubstituierter O, O-Dimethyl-O-phenyl-phospate and thiophosphate" Journal Für Praktische Chemie, vol. 317, No. 5, 1975, pp. 721-732.
Kilby et al., "The inhibition of trypsin and chymotrypsin by certain organic phosphorous esters," Biochemical Journal, vol. 57, 1954, pp. 303-309.
Law et al., "Dialkyl phenyl phosphates as novel selective inhibitors of butyrylcholinesterase," Biochemical and Biophysical Research Communications, vol. 355, No. 2, 2007, pp. 371-378.
Law et al., "Differential inhibition of acetylcholinesterase and butyrylcholinesterase by dialkyl phenyl phosphates," FASEB Journal, vol. 18, No. 8, 2004, Suppl. S., pp. C140-C141.
Law et al., "Differential inhibition of acetylcholinesterase and butyrylcholinesterase by phosphotriesters," Abstracts, 38th Western Regional Meeting of the American Chemical Society, Long Beach, CA, United States, Oct. 15-18, 2003, Publisher: American Chemical Society, Washington D.C.
Mager et al., "Structure-activity relationships applied to phenyl diethyl phosphate pesticides," Pharmazie, vol. 37, No. 10, 1982, pp. 729-730.
Nagamatsu et al., "New phosphorylating agents for general synthesis of mixed phosphate esters" Tetrahedron Letters, vol. 38, No. 21, 1987, pp. 2375-2378.
Nakayama et al., "Differential inhibition of acetylcholinesterase and butyrylcholinesterase by phosphotriesters," Abstracts of Papers, 227th American Chemical Society National Meeting, Anaheim, CA, United States, Mar. 28-Apr. 1, 2004, CHED-926.
Patani et al., "Bioisosterism: a rational approach in drug design," Chem. Rev., vol. 96, 1996, pp. 3147-3176.
Pruett et al., "A comparative study of inhibition of acetylcholinesterase, trypsin, neuropathy target esterase, and spleen cell activation by structurally related organophosphorus compounds," Journal of Biochemical Toxicology, vol. 9, No. 6, 1994, pp. 319-327.
Siddall et al., "Conformation of Organophosphorus Compounds. II. Proton Magnetic Resonance Studies of Some Phosphites, Phosphonites, Phosphates, Phosphonates and Additional Phosphinates," Journal of the American Chemical Society., vol. 84, No. 18, 1962, pp. 3467-3473.
Thau-Alexandrowicz et al., "Viscosity study of certain alkyl phosphates and their aqueous mixtures," Journal of Chemical and Engineering Data, vol. 17, No. 3, 1972, pp. 339-341.
Van Hooidonk et al., "On the reactivity of organophosphorus compounds. Part III. Application of the Hammett relation to the rates of alkaline hydrolysis of a number, of diethyl substituted phenyl phosphates," Recueil Des Travaux Chimiques Des Pays-Bas, vol. 86, 1967, pp. 449-457.
DiResta et al., "Measurement of Brain Tissue Density Using Pycnometry," Brain Edema VIII, pp. 34-36, DOI: 10.1007/978-3-7091-9115-6_12.
Ghang et al., "Selective Cavitand-Mediated Endocytosis of Targeted Imaging Agents into Live Cells," J. Am. Chem. Soc., 2013, 135 (19), pp. 7090-7093; DOI: 10.1021/ja401273g.

* cited by examiner

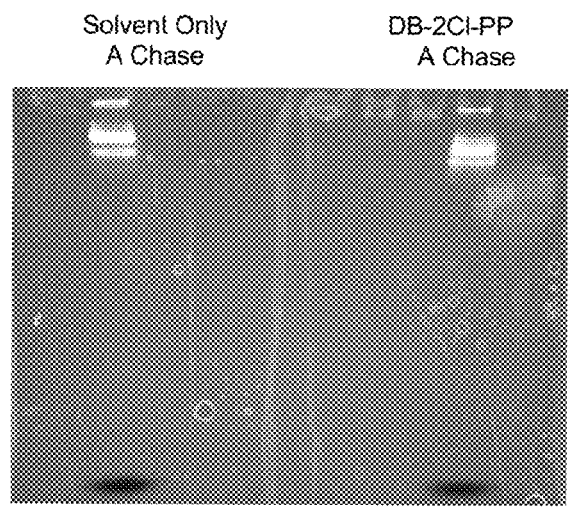
FIGURE 1
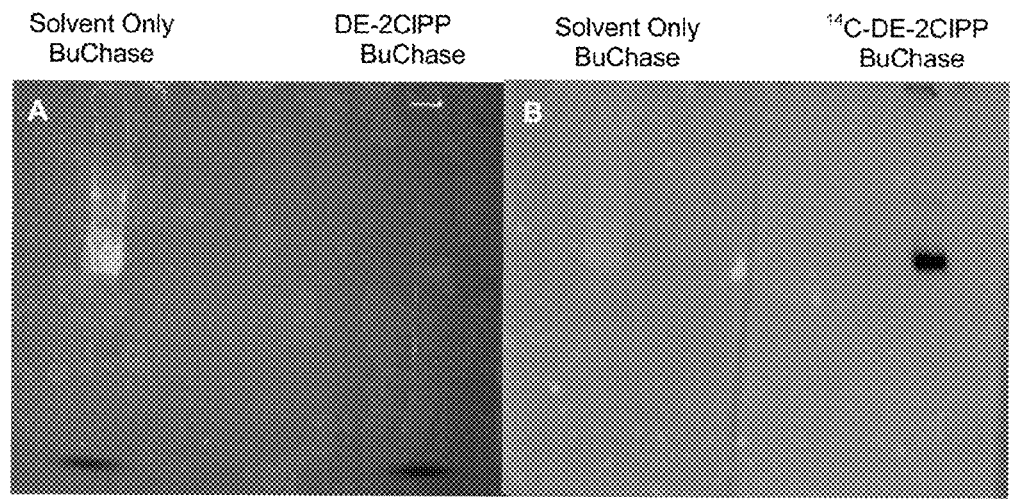
FIGURE 2A         FIGURE 2B

Effect of DB2ClPP on the Activity of Trypsin.

Effect of DB2ClPP on the Activity of Chymotrypsin.

Effect of DB2ClPP on Hexokinase Activity.

BUTYRYLCHOLINESTERASE INHIBITORS

CROSS REFERENCE TO RELATED APPLICATION

This application is a continuation-in-part of U.S. patent application Ser. No. 14/71,871, filed Nov. 5, 2013, which is a continuation-in-part of U.S. patent application Ser. No. 12/447,862, filed Apr. 29, 2009, and is a continuation-in-part of U.S. patent application Ser. No. 12/447,862, filed Apr. 29, 2009, which is a 371 application of International Patent Application No. PCT/US2007/083262, filed Oct. 31, 2007, which claims the benefit of U.S. Provisional Patent Application No. 60/863,764, filed Oct. 31, 2006, the disclosures of which are hereby incorporated by reference in their entireties.

FIELD OF THE INVENTION

The present disclosure relates to inhibitors of butyrylcholinesterase.

BACKGROUND OF THE INVENTION

Neurodegenerative diseases result from deterioration of neurons which over time will lead to neurodegeneration and disabilities.

It is known that reduction in levels of acetylcholine parallels the severity of a neurodegenerative disorder such as Alzheimer's disease (AD). In addition, progression of AD occurs concomitantly with changes in cholinesterase activity, i.e., acetylcholinesterase activity (AcChase) decreases while butyrylcholinesterase (BuChase) activity increases. Since both enzymes hydrolyze acetylcholine, the treatment for AD is based on the assumption that inhibiting the activity of these enzymes, in particular butyrylcholinesterase, will increase the level of acetylcholine. Unfortunately, currently utilized cholinesterase inhibitors are non-specific and show adverse peripheral effects.

Several neurodegenerative disorders are also associated with the formation of beta-amyloid plaques. They seem to be formed in the brain many years before the clinical signs of the disorder, e.g. AD, are detectable. Beta-amyloid plaque formation is associated with BuChase activity. Therefore, BuChase inhibitors can have a significant effect on preventing or retarding the formation of beta-amyloid plaques.

In addition, there is a general need for BuChase specific inhibitors. These compounds may be used in various biochemical, pharmacological, and cell biology applications to study the role of BuChase in normal cell growth and development, e.g., stem cell differentiation. Therefore, there is an unmet need for specific inhibitors of butyrylcholinesterase.

SUMMARY OF THE INVENTION

One aspect of the disclosure relates to inhibitors of butyrylcholinesterase for the treatment of neurodegenerative diseases. These inhibitors have the following general formulas:

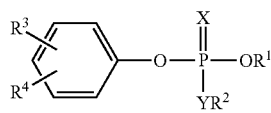

Formula 1

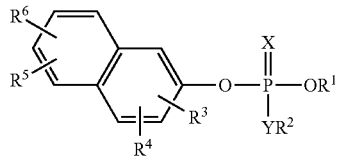

Formula 2 wherein
X is O or S;
Y is O or N;
$R^1$ and $R^2$ can be the same or different and are independently selected from the group consisting of H, $C_1$-6 alkyl, $C_1$-6 alkenyl, and unsubstituted or substituted phenyl;
$R^3$ to $R^6$ can be the same or different and are independently selected from the group consisting of H, methyl, methoxy, and at least one electron withdrawing group;
or a pharmaceutically acceptable salt thereof.

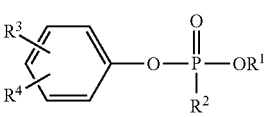

Formula 3

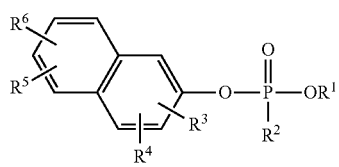

Formula 4 wherein
$R^1$ and $R^2$ can be the same or different and are independently selected from the group consisting of H, $C_1$-6 alkyl, $C_1$-6 alkenyl, and unsubstituted or substituted phenyl;
$R^3$ to $R^6$ can be the same or different and are independently selected from the group consisting of H, methyl, methoxy, and at least one electron withdrawing group;
or a pharmaceutically acceptable salt thereof.

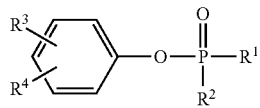

Formula 5

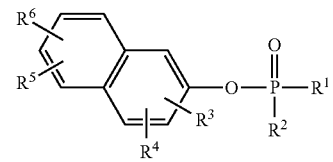

Formula 6 wherein
$R^1$ and $R^2$ can be the same or different and are independently selected from the group consisting of H, $C_1$-6 alkyl, $C_1$-6 alkenyl and unsubstituted or substituted phenyl;
$R^3$ to $R^6$ can be the same or different and are independently selected from the group consisting of H, methyl, methoxy, and at least one electron withdrawing group;
or a pharmaceutically acceptable salt thereof.

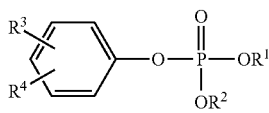

Formula 7 wherein

R¹ and R² can be the same or different and are independently selected from the group consisting of H, methyl, ethyl, n-propyl, isopropyl, n-butyl, isobutyl, n-pentyl, and unsubstituted or substituted phenyl;

R³ and R⁴ can be the same or different and are independently selected from H or at least one electron withdrawing group;

or a pharmaceutically acceptable salt thereof.

Another aspect of the disclosure relates to pharmaceutical compositions containing a pharmaceutical carrier and a therapeutically effective amount of these inhibitors of butyrylcholinesterase.

Another aspect of the disclosure relates to methods of treating a neurodegenerative disease by administering a therapeutically effective amount of these inhibitors of butyrylcholinesterase.

BRIEF DESCRIPTION OF THE DRAWINGS

FIG. 1 depicts the effect of di-n-butyl 2-chlorophenyl phosphate (DB2ClPP) on acetylcholinesterase (AcChase) activity. AcChase was pre-incubated with either solvent or di-n-butyl 2-chlorophenyl phosphate, fractionated by native gel electrophoresis, and stained for enzyme activity.

FIGS. 2A and 2B depict phosphorylation of butyrylcholinesterase by di-ethyl 2-chlorophenyl phosphate. Butyrylcholinesterase was incubated with $^{14}$C-labeled diethyl 2-chloro phenyl phosphate, or solvent, then separated using native PAGE. A) Gel stained for enzyme activity. B) Autoradiography of the gel.

DETAILED DESCRIPTION OF THE INVENTION

Figure 3:
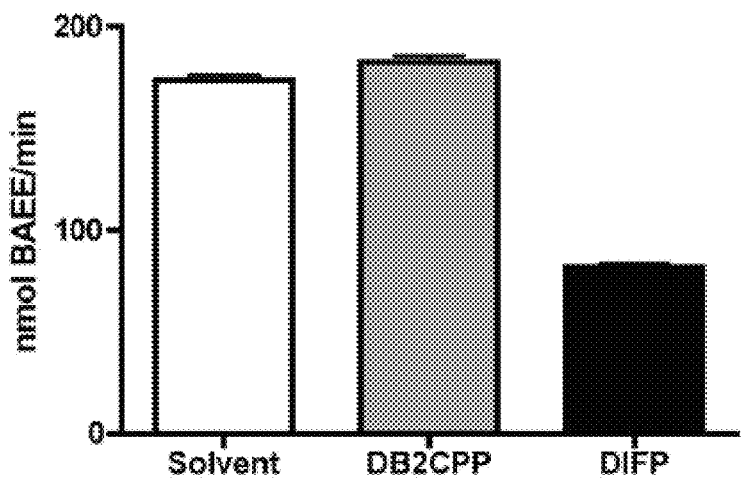
FIG. 3 depicts the effect of DB2ClPP on the activity of trypsin.

One aspect of the disclosure relates to inhibitors of butyrylcholinesterase (BuChase).

The butyrylcholinesterase inhibitors can be represented by a compound of Formula 1 or Formula 2

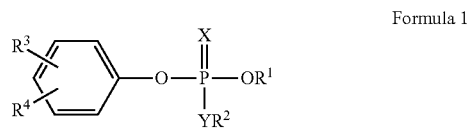

Formula 1

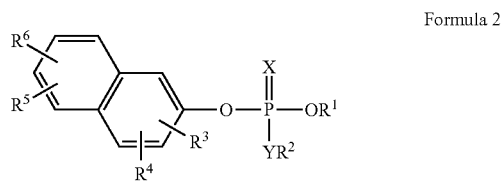

Formula 2 wherein

X is O or S;

Y is O or N;

R¹ and R² can be the same or different and are independently selected from the group consisting of H, C₁-6 alkyl, C₁-6 alkenyl, and unsubstituted or substituted phenyl;

R³ to R⁶ can be the same or different and are independently selected from the group consisting of H, methyl, methoxy, and at least one electron withdrawing group; or a pharmaceutically acceptable salt thereof.

Alternatively, when R¹ and/or R² is phenyl, the phenyl may be substituted at least once wherein each substituent is independently selected from the group consisting of H, methyl, methoxy, and at least one electron withdrawing group.

Alternatively, the C₁-6 alkyl is selected from the group consisting of methyl, ethyl, n-propyl, isopropyl, n-butyl, isobutyl, cyclohexyl and n-pentyl.

Exemplary compounds of Formulas 1 and 2 include but are not limited to:

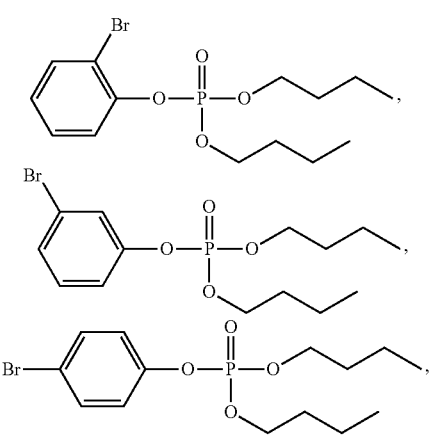

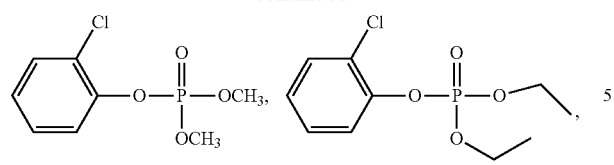
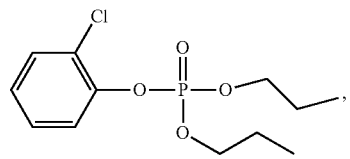
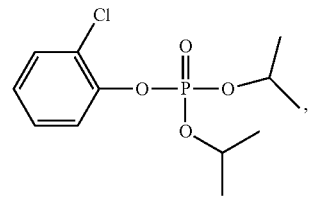
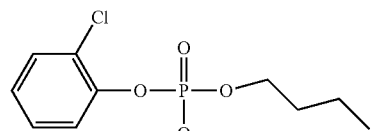
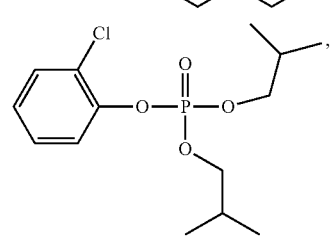
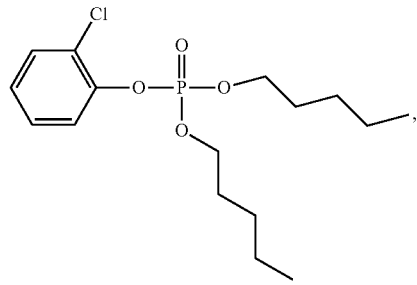
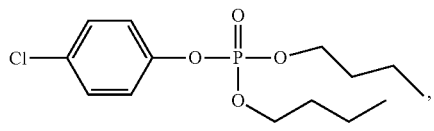
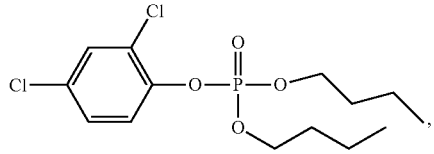
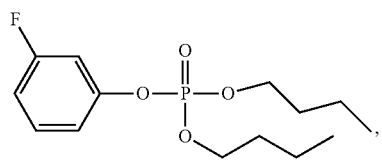
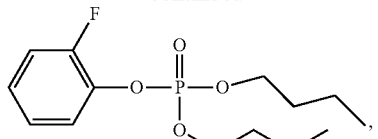
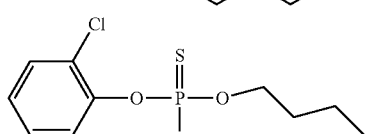
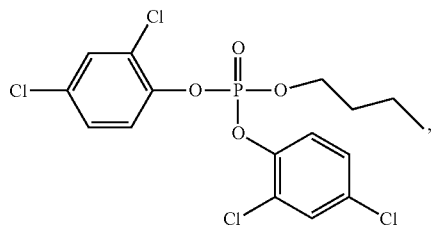
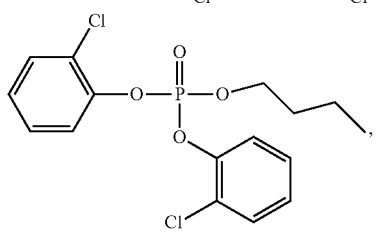
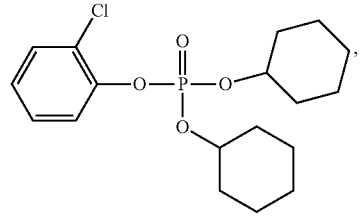
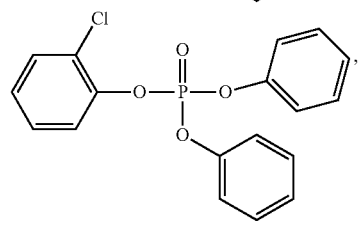
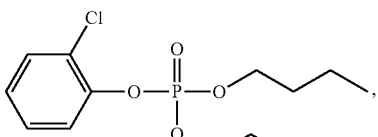
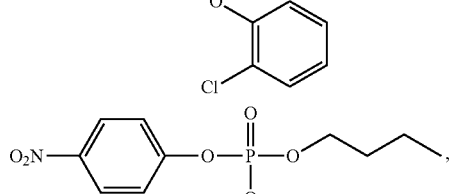
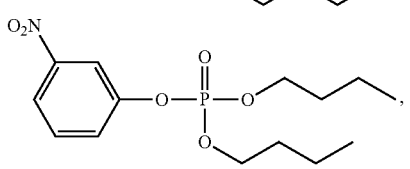

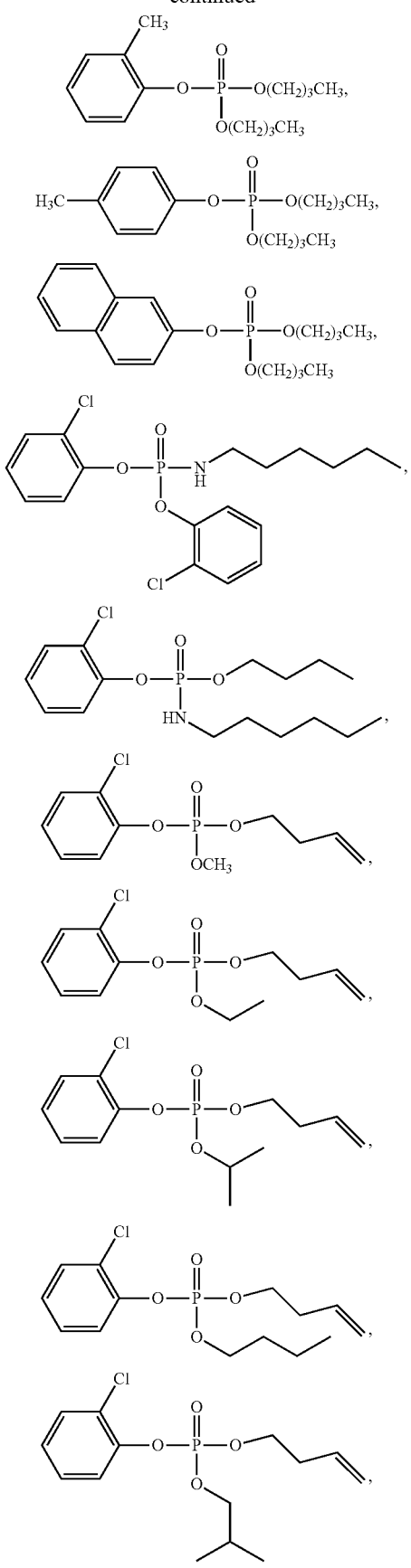

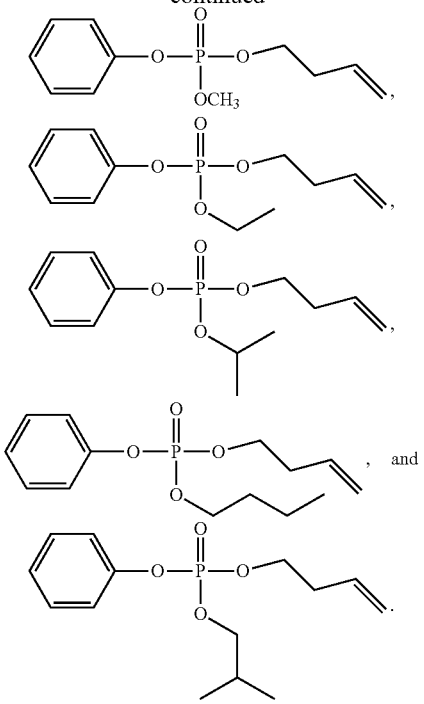

The butyrylcholinesterase inhibitors can also be represented by a compound of Formulas 3 and 4

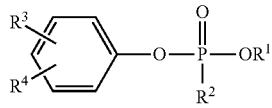
Formula 3

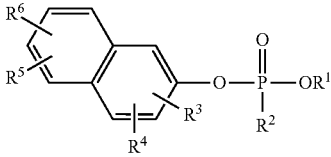
Formula 4 wherein $R^1$ and $R^2$ can be the same or different and are independently selected from the group consisting of H, $C_1$-6 alkyl, $C_1$-6 alkenyl, and unsubstituted or substituted phenyl;

$R^3$ to $R^6$ can be the same or different and are independently selected from the group consisting of H, methyl, methoxy, and at least one electron withdrawing group;

or a pharmaceutically acceptable salt thereof.

Alternatively, when $R^1$ and/or $R^2$ is phenyl, the phenyl may be substituted at least once wherein each substituent is independently selected from the group consisting of H, methyl, methoxy, and at least one electron withdrawing group.

Alternatively, the $C_1$-6 alkyl is selected from the group consisting of methyl, ethyl, n-propyl, isopropyl, n-butyl, isobutyl, cyclohexyl and n-pentyl.

Exemplary compounds of Formulas 3 and 4 include but are not limited to:

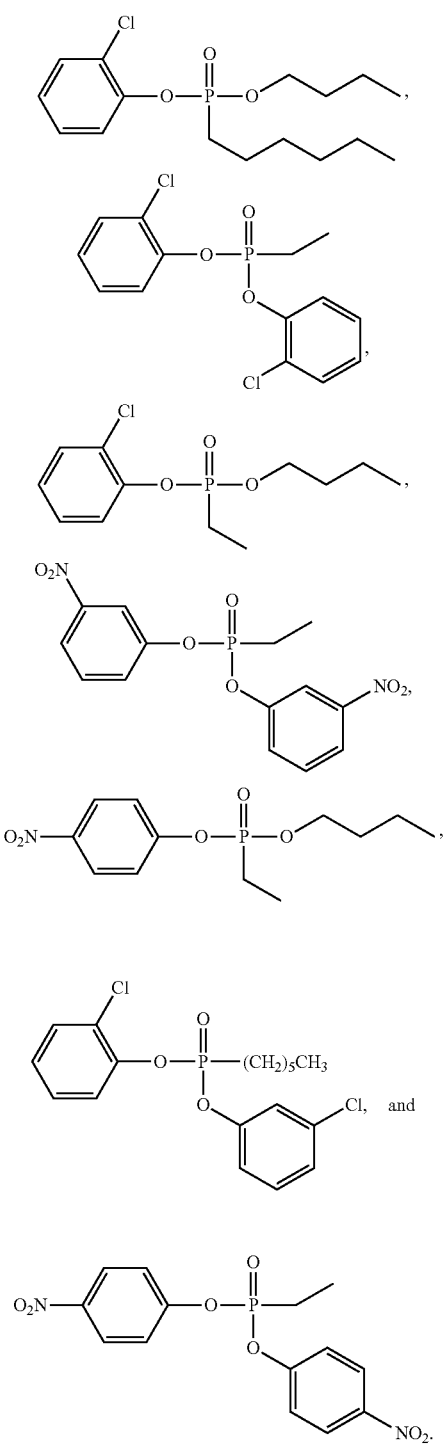

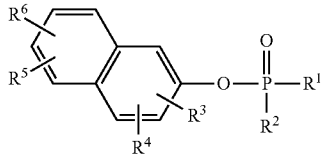

wherein $R^1$ and $R^2$ can be the same or different and are independently selected from the group consisting of H, $C_1$-6 alkyl, $C_1$-6 alkenyl, and unsubstituted or substituted phenyl;

$R^3$ to $R^6$ can be the same or different and are independently selected from the group consisting of H, methyl, methoxy, and at least one electron withdrawing group;

or a pharmaceutically acceptable salt thereof.

Alternatively, when $R^1$ and/or $R^2$ is phenyl, the phenyl may be substituted at least once wherein each substituent is independently selected from the group consisting of H, methyl, methoxy, and at least one electron withdrawing group.

Alternatively, the $C_1$-6 alkyl is selected from the group consisting of methyl, ethyl, n-propyl, isopropyl, n-butyl, isobutyl, cyclohexyl and n-pentyl.

Exemplary compounds of Formulas 5 and 6 include but are not limited to:

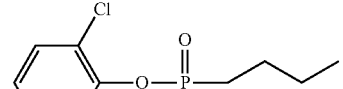

The butyrylcholinesterase inhibitors can also be represented by a compound of Formula 7

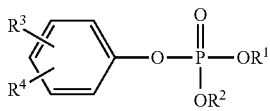

Formula 7 wherein $R^1$ and $R^2$ can be the same or different and are independently selected from the group consisting of H, methyl, ethyl, n-propyl, isopropyl, n-butyl, isobutyl, n-pentyl, and unsubstituted or substituted phenyl $R^3$ and $R^4$ can be the same or different and are independently selected from H or at least one electron withdrawing group;

or a pharmaceutically acceptable salt thereof.

Alternatively, when $R^1$ and/or $R^2$ is phenyl, the phenyl may be substituted at least once wherein each substituent is independently selected from H or at least one electron withdrawing group.

An "electron withdrawing group" draws electrons away from a reaction center. Electron withdrawing groups as defined herein include but are not limited to halogens, nitriles, carboxylic acids and carbonyls. Specific examples of electron withdrawing groups include but are not limited to F, Cl, Br, I, and $NO_2$.

A "pharmaceutically acceptable salt" as used herein is any salt that retains at least some of the activity of the parent compound and without imparting any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

Another aspect of the present disclosure is drawn to therapeutic compositions comprising the presently disclosed compounds and a pharmaceutically acceptable carrier. The carrier may be any solid, semi-solid, or liquid material that acts as an excipient or vehicle for the active compound. The formulations may also include wetting agents, emulsifying agents, preserving agents, sweetening agents, bulking agents, coatings and/or flavoring agents. If used in an ophthalmic or infusion format, the formulation will usually contain one or more salts to adjust the osmotic pressure of the formulation.

The present disclosure provides for inhibitors of butyrylcholinesterase for use in the treatment of a condition or disease which is ameliorated by cholinesterase inhibition. Without wishing to be bound by theory, one of the ways cholinesterase inhibition can be helpful in the treatment of a neurodegenerative disease is by eliminating, reducing, or preventing the formation of beta amyloid plaques.

The diseases or conditions which can be treated by the presently disclosed inhibitors of butyrylcholinesterase include neurodegenerative diseases including, but not limited to, Alzheimer's disease and Lou Gehrig's disease.

Some embodiments include a method of treating Alzheimer's disease, comprising administering a compound described herein, such as DB2ClPP, to a mammal in need thereof.

Some embodiments include a method of reducing the level of a β-amyloid peptide in a brain of a mammal comprising administering an effective amount of a compound described herein, such as DB2ClPP, to the mammal. In some embodiments, the β-amyloid peptide is Aβ40. For example, the level of Aβ40 in the brain of the mammal can be reduced by at least about 10%, at least about 20%, or at least about 30%. In some embodiments, the β-amyloid peptide is Aβ42. For example, the level of Aβ42 in the brain of the mammal can be reduced by at least about 10%, at least about 20%, or at least about 30%.

For any method described herein, such as treating Alzheimer's disease in a mammal, or reducing the level of a β-amyloid peptide in a brain of a mammal, the mammal can be a human being that is at least about 50 years of age, at least about 65 years of age, at least about 70 years of age, at least about 75 years of age, at least about 80 years of age, or at least about 85 years of age.

One of ordinary skill in the art also will recognize that the presently disclosed butyrylcholinesterase inhibitors may be generally useful for performing various chemical, biochemical, pharmacological and cellular studies. For example, it may be useful to knock out the activity of butyrylcholinesterase by using the presently disclosed inhibitors and observing the effects. The presently disclosed compounds may be useful in stem cell research.

The present disclosure also provides for methods of treating neurodegenerative diseases with a therapeutically effective amount of a butyrylcholinesterase inhibitor.

Thus, the compounds of the present disclosure may be formulated for oral, buccal, transdermal (e.g., patch), intranasal, parenteral (e.g., intravenous, intramuscular or subcutaneous), ophthalmic or rectal administration or in a form suitable for administration by inhalation or insufflation.

For oral administration, the compounds may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycollate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the compounds may take the form of tablets or lozenges formulated in conventional manner.

The compounds of the present disclosure may be formulated for parenteral administration by injection, including using conventional catheterization techniques or infusion. The compounds may also be formulated for topical ophthalmic administration.

Formulations for injection or topical ophthalmic administration may be presented in unit dosage form, for example in ampules, or in multi-dose containers, optionally with an added preservative. The compounds may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The compounds of the present disclosure may also be formulated in rectal compositions such as suppositories or retention enemas, e.g., containing conventional suppository bases such as cocoa butter or other glycerides.

For intranasal administration or administration by inhalation, the compounds of the present disclosure are conveniently delivered in the form of a solution or suspension from a pump spray container that is squeezed or pumped by the patient. The compounds of the disclosure can also be delivered in the form of an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the disclosure and a suitable powder base such as lactose or starch.

As used herein, the term "effective amount" means an amount of a compound of the present disclosure that is capable of inhibiting the symptoms of a pathological condition described herein by modulation of butyrylcholinesterase activity. The specific dose of a compound administered according to the present disclosure will be determined by the particular circumstances such as the compound administered, the route of administration, the state of being of the patient, and the severity of the pathological condition. A proposed dose of a compound of the present disclosure for oral, parenteral, buccal or topical ophthalmic administration to the average adult human for the treatment of the conditions referred to above is about 0.01 to 50 mg/kg of the active ingredient per unit dose which could be administered, for example, 1 to 4 times per day.

In some embodiments, a compound described herein, such as DB2ClPP, is administered orally in an effective amount. For example, in some embodiments, an effective amount in a dosage form can be at least about 0.1 mg, at least about 1 mg, at least about 2 mg, at least about 5 mg, or at least about 10 mg, up to about 100 mg, up to about 200 mg, up to about 300 mg, up to about 400 mg, or up to about 500 mg, of the compound.

The potential as a therapeutic for Alzheimer's disease, or other conditions, may be improved if the compound in question is able to cross the blood brain barrier. In some embodiments, a sufficient amount of a compound described herein, such as DB2ClPP, is administered so that at least about 10 ng, at least about 50 ng, at least about 100 ng, up to about 1 µg, up to about 1 mg, or up to about 100 mg, of the compound crosses the blood brain barrier.

In some embodiments, sufficient amount of a compound described herein, such as DB2ClPP, is administered so that the compound has a concentration of at least about $10^{-10}$ M at least about $10^{-9}$ M, at least about $10^{-8}$ M, up to about $10^{-6}$ M, or up to about $10^{-5}$ M, in the brain.

Aerosol formulations for treatment of the conditions referred to above in the average adult human are preferably arranged so that each metered dose or "puff" of aerosol contains 20 µg to 1000 µg of the compound of the disclosure. The overall daily dose with an aerosol will be within the range a 100 µg to 10 mg. Administration may be several times daily, for example 2, 3, 4 or 8 times, giving for example, 1, 2 or 3 doses each time.

EXAMPLES

Example 1: Synthesis

Method A
Representative Procedure for Method A.

To a dry 50 mL round bottom flask were added 10 mL of $CH_2Cl_2$ and 1.3 mL (2.0 g, 8.2 mmol) of 2-chlorophenyl dichlorophosphate. The solution was cooled to 0° C. using an ice water bath. Then 2.5 equivalents of alcohol and 2.5 equivalents of pyridine in 10 mL of $CH_2Cl_2$ were added to the stirring solution via cannulation. The reaction was left to stir overnight at room temperature. The reaction mixture was diluted with 80 mL of diethyl ether and washed three times with 40 mL of 10% HCl. The aqueous layers were combined and washed with 40 mL of $CH_2Cl_2$. The combined organic layer was washed once with 40 mL of saturated sodium bicarbonate, dried over magnesium sulfate, filtered, concentrated in vacuo, and purified by evaporative distillation.

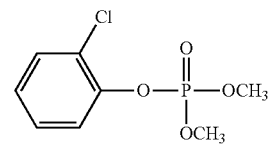

2-Chlorophenyl dimethyl phosphate

Following the representative procedure described above and using methanol, 2-chlorophenyl dimethyl phosphate was obtained as a clear oil: 80% yield; b.p. 183° C./0.2 mm Hg; $^1$H NMR (400 MHz, CDCl$_3$) δ 3.92 (d, 6H, 11.4 Hz, CH$_3$), 7.11-7.15 (m, 1H, Ar—H), 7.52 (td, 1H, 8.2, 1.7 Hz, Ar—H), 7.41-7.42 (m, 1H, Ar—H), 7.43-7.44 (m, 1H, Ar—H); $^{13}$C NMR (100 MHz, CDCl$_3$) δ 55.22, 55.28, 121.32, 121.34, 125.30, 125.38, 126.03, 128.02, 128.03, 130.65, 146.59, 146.65.

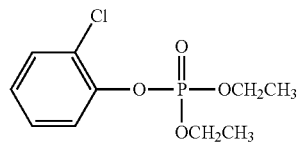

2-Chlorophenyl diethyl phosphate

Following the representative procedure described above and using ethanol, 2-chlorophenyl diethyl phosphate was obtained as a clear oil: 100% yield; b.p. 180° C./0.3 mm Hg; $^1$H NMR (400 MHz, CDCl$_3$) δ 1.37 (td, 6H, 7.1, 1.1 Hz, CH$_3$), 4.23-4.32 (m, 4H, CH$_2$), 7.09-7.13 (m, 1H, Ar—H), 7.24 (td, 1H, 8.2, 1.7 Hz, Ar—H), 7.41 (dt, 1H, 7.9, 1.4 Hz, Ar—H), 7.45 (dt, 1H, 8.2, 1.3 Hz, Ar—H); $^{13}$C NMR (100 MHz, CDCl$_3$) δ 16.00, 16.03, 16.07, 16.10, 64.97, 65.03, 121.32, 121.35, 125.32, 125.39, 125.76, 127.88, 127.89, 130.57, 146.77, 146.83.

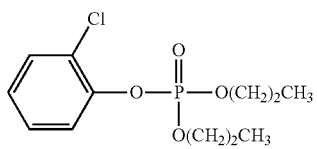

2-Chlorophenyl di-n-propyl phosphate

Following the representative procedure described above and using n-propanol, 2-chlorophenyl di-n-propyl phosphate was obtained as a clear oil: 82% yield; b.p. 245° C./0.3 mm Hg; $^1$H NMR (400 MHz, CDCl$_3$) δ 0.96 (t, 6H, 7.4 Hz, CH$_3$), 1.74 (sextet, 4H, 7.3 Hz, CH$_2$CH$_2$CH$_3$), 4.11-4.21 (m, 4H, CH$_2$CH$_2$CH$_3$), 7.08-7.13 (m, 1H, Ar—H), 7.24 (td, 1H, 8.2, 1.7 Hz, Ar—H), 7.41 (dt, 1H, 7.9, 1.3 Hz, Ar—H), 7.46 (dt, 1H, 8.2, 1.3 Hz, Ar—H); $^{13}$C NMR (100 MHz, CDCl$_3$) δ 9.94, 23.56, 23.62, 70.37, 70.44, 121.33, 121.35, 125.34, 125.41, 125.71, 125.73, 127.87, 127.88, 130.55, 146.82, 146.89.

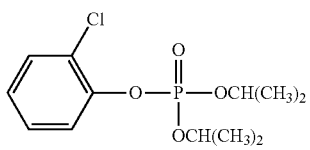

2-Chlorophenyl di-i-propyl phosphate

Following the general procedure described above and using i-propanol, 2-chlorophenyl di-i-propyl phosphate was obtained as a clear oil: 70% yield; b.p. 205° C./0.7 mm Hg; $^1$H NMR (400 MHz, CDCl$_3$) δ 1.33 (d, 6H, 6.2 Hz, CH$_3$), 1.38 (d, 6H, 6.2 Hz, CH$_3$), 4.81 (sept of doublets, 2H, 6.3, 0.8 Hz, CH(CH$_3$)$_2$), 7.09 (tm, 1H, 8.0 Hz, Ar—H), 7.23 (td, 1H, 8.2, 1.6 Hz, Ar—H), 7.40 (dt, 1H, 7.9, 1.5 Hz, Ar—H), 7.49 (dt, 1H, 8.2, 1.4 Hz, Ar—H); $^{13}$C NMR (100 MHz, CDCl$_3$) δ 23.45, 23.47, 23, 50, 23.52, 23.62, 23.64, 23.67, 23.69, 73.94, 74.00, 121.19, 121.21, 125.27, 125.35, 125.43, 127.75, 127.76, 130.48, 147.01, 147.07.

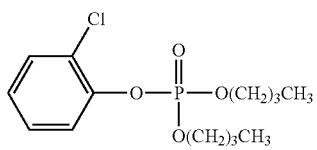

Di-n-butyl 2-chlorophenyl phosphate

Following the general procedure described above and using n-butanol, 2-chlorophenyl di-n-butyl phosphate was obtained as a clear oil: 52% yield; b.p. 205° C./0.6 mm Hg; $^1$H NMR (400 MHz, CDCl$_3$) δ 0.92 (t, 6H, 7.4 Hz, CH$_3$), 1.36-1.45 (m, 4H, 6.2, CH$_2$CH$_2$CH$_2$CH$_3$), 1.65-1.72 (m, 4H, 6.3, CH$_2$CH$_2$CH$_2$CH$_3$), 4.15-4.25 (m, 4H, CH$_2$CH$_2$CH$_2$CH$_3$), 7.09-7.13 (m, 1H, Ar—H), 7.24 (td, 1H, 8.2, 1.6 Hz, Ar—H), 7.41 (dt, 1H, 8.0, 1.4 Hz, Ar—H), 7.45 (dt, 1H, 8.2, 1.3 Hz, Ar—H); $^{13}$C NMR (100 MHz, CDCl$_3$) δ 13.53, 18.59, 32.13, 32.20, 68.62, 68.69, 121.32, 121.34, 125.33, 125.41, 125.68, 127.83, 127.84, 130.54, 146.82, 146.88.

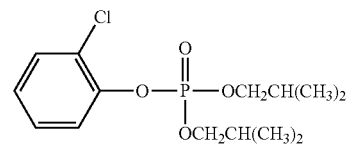

Di-i-butyl 2-Chlorophenyl phosphate

Following the general procedure described above and using i-butanol, di-i-butyl 2-chlorophenyl phosphate was obtained as clear oil: 40% yield; b.p. 179° C./0.7 mm Hg; $^1$H NMR (400 MHz, CDCl$_3$) δ 0.95 (appt dd, 12H, 6.7, 1.1 Hz, CH$_3$), 1.99 (septet, 2H, 6.6 Hz, CH), 3.92-4.01 (m, 4H, CH$_2$), 7.08-7.13 (m, 1H, Ar—H), 7.24 (td, 1H, 8.1, 1.7 Hz, Ar—H), 7.41 (dt, 1H, 8.0, 1.4 Hz, Ar—H), 7.46 (dt, 1H, 8.2, 1.2 Hz, Ar—H); $^{13}$C NMR (100 MHz, CDCl$_3$) δ 18.57, 18.59, 18.60, 29.02, 29.09, 74.67, 74.73, 121.37, 121.40, 125.37, 125.44, 125.71, 127.87, 127.88, 130.56, 146.86, 146.91.

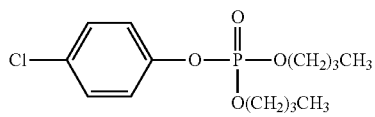

Di-n-butyl 4-chlorophenyl phosphate

Following the general procedure described above using dichloro 4-chlorophenylphosphate and n-butanol, di-n-butyl 4-chlorophenyl phosphate was obtained as a clear oil: 84%; b.p. 200° C./0.2 mm Hg; $^1$H NMR (400 MHz, CDCl$_3$) δ 0.92 (t, 6H, 7.3 Hz, CH$_3$), 1.35-1.4 (m, 4H, CH$_2$CH$_2$CH$_2$CH$_3$), 1.67 (quintet, 4H, 6.7 Hz, CH$_2$CH$_2$CH$_2$CH$_3$), 4.09-4.20 (m, 4H, CH$_2$CH$_2$CH$_2$CH$_3$), 7.15-7.18 (m, 2H, Ar—H), 7.28-7.31 (m, 1H, Ar—H); $^{13}$C NMR (100 MHz, CDCl$_3$) δ 13.41, 18.51, 32.06, 32.13, 68.31, 68.36, 121.24, 129.57, 130.15, 130.16, 149.23, 149.31.

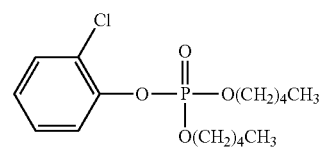

2-Chlorophenyl di-n-pentyl phosphate

Following the general procedure described above and using n-pentanol, 2-chlorophenyl di-n-pentyl phosphate was obtained as a clear oil: 88%; b.p. 185° C./0.3 mm Hg; $^1$H NMR (400 MHz, CDCl$_3$) δ 0.89 (t, 6H, 7.2 Hz, CH$_3$), 1.27-1.39 (m, 8H, CH$_2$CH$_2$CH$_3$), 1.67-1.74 (m, 4H, CH$_2$CH$_2$CH$_2$CH$_3$), 4.14-4.24 (m, 4H, CH$_2$CH$_2$CH$_2$CH$_3$), 7.08-7.13 (m, 1H, Ar—H), 7.24 (td, 1H, 8.2, 1.6 Hz, Ar—H), 7.41 (dt, 1H, 7.9, 1.4 Hz, Ar—H), 7.46 (dt, 1H, 8.2, 1.3 Hz, Ar—H); $^{13}$C NMR (100 MHz, CDCl$_3$) δ 13.93, 22.17, 27.48, 29.84, 29.90, 68.93, 69.00, 121.33, 121.35, 125.34, 125.41, 125.68, 125.70, 127.85, 127.87, 130.54, 146.81, 146.87.

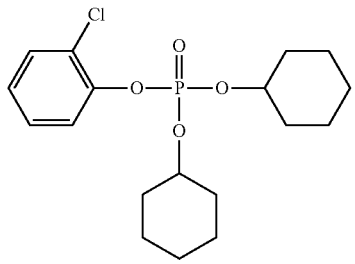 [SMILES: O=P(Oc1ccccc1Cl)(OC1CCCCC1)OC1CCCCC1]

2-chlorophenyl dicyclohexyl phosphate

Following the general procedure described above and using cyclohexanol, the crude product was purified by gravity column chromatography (silica gel 1:1, hexane:EtOAc), a second gravity column chromatography (silica gel 7:3, hexane:EtOAc) and evaporative distillation (b.p. 260° C./0.10 mm Hg) to afford 2-chlorophenyl dicyclohexyl phosphate as a colorless oil: 70% yield; $^1$H NMR (400 MHz, CDCl$_3$) δ 1.21-1.98 (m, 20H, (OCHC$_5$H$_{12}$), 4.50-4.59 (m, 2H, (OCH)$_2$), 7.06-7.11 (m, 1H, Ar—H), 7.20-7.25 (m, 1H, Ar—H), 7.38-7.41 (m, 1H, Ar—H), 7.47-7.50 (m, 1H, Ar—H); $^{13}$C NMR (100 MHz, CDCl$_3$) δ 23.32, 25.01, 32.97, 33.02, 33.15, 33.19, 78.40, 78.47, 121.16, 121.18, 125.22, 125.31, 127.65, 127.66, 130.37, 147.01, 147.07.

Method B

Representative Procedure for Method B.

A solution of dibutyl phosphite (0.73 g, 3.8 mmol) in 3 mL CCl$_4$ was added dropwise to a stirring solution containing the substituted phenol (3.0 mmol), 5 mL CCl$_4$, tetra-n-butylammonium bromide (0.095 g, 0.3 mmol), NaOH (0.18 g, 4.4 mmol) and 5 mL water; it was stirred for an indicated amount of time at room temperature. The reaction mixture was dissolved in 10 mL of CCl$_4$, extracted with ice-cold distilled water (3×10 mL), and each of the aqueous layer was washed with 10 mL CCl$_4$. The combined organic layer was dried under MgSO$_4$, concentrated in vacuo, and purified by evaporative distillation, flash or gravity chromatography.

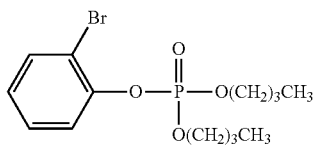

2-Bromophenyl di-n-butyl phosphate

Following the representative procedure described above using 2-bromophenol (2 hours reaction time), the crude product was purified by evaporative distillation (b.p. 175° C./0.45 mmHg) followed by flash chromatography (silica gel, hexane:EtOAc, 3:2) to give 2-bromophenyl di-n-butyl phosphate as a pale yellow oil: 56% yield; R$_f$=0.49 (hexane:EtOAc, 1:1); $^1$H NMR (400 MHz, CDCl$_3$) δ 0.92 (t, J=7.4 Hz, 6H, CH$_2$CH$_2$CH$_2$CH$_3$), 1.36-1.46 (m, 4H, CH$_2$CH$_2$CH$_2$CH$_3$), 1.65-1.73 (m, 4H, CH$_2$CH$_2$CH$_2$CH$_3$), 4.17-4.26 (m, 4H, CH$_2$CH$_2$CH$_2$CH$_3$), 7.02-7.06 (m, 1H, Ar—H), 7.27-7.31, 1H, Ar—H), 7.47 (dt, J=8.2 Hz, 1.3 Hz, 1H, Ar—H), 7.58 (dt, J=8.0 Hz, 1.4 Hz, 1H, Ar—H); $^{13}$C NMR (100 MHz, CDCl$_3$) δ 13.46, 18.54, 32.07, 32.14, 68.61, 68.68, 114.29, 114.38, 120.99, 121.01, 125.93, 128.55, 128.56, 133.54, 147.87, 147.93.

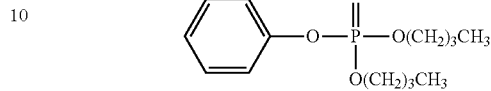

3-Bromophenyl n-butyl phosphate

Following the representative procedure described above using 3-bromophenol, the crude product was purified by gravity chromatography (silica gel, hexane:EtOAc, 4:1) to give 3-bromophenyl di-n-butyl phosphate as a clear oil: 38% yield; R$_f$=0.5 (hexane:EtOAc, 1:1); $^1$H NMR (400 MHz, CDCl$_3$) δ 0.93 (t, J=7.4 Hz, 6H, OCH$_2$CH$_2$CH$_2$CH$_3$), 1.36-1.45 (m, 4H, OCH$_2$CH$_2$CH$_2$CH$_3$), 1.64-1.71 (m, 4H, OCH$_2$CH$_2$CH$_2$CH$_3$), 4.10-4.20 (m, 4H, OCH$_2$CH$_2$CH$_2$CH$_3$), 7.16-7.23 (m, 2H, Ar—H), 7.30-7.33 (m, 1H, Ar—H), 7.39-7.40 (m, 1H, Ar—H); $^{13}$C NMR (400 MHz, CDCl$_3$) δ 13.49, 13.50, 18.58, 32.12, 32.19, 68.45, 68.51, 118.75, 118.80, 122.56, 123.47, 123.52, 128.16, 130.70, 151.21, 151.28.

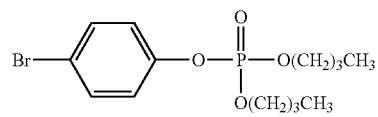

4-Bromophenyl di-n-butyl phosphate

Following the representative procedure described above using 4-bromophenol, the crude product was purified by gravity chromatography (silica gel, 4:1, hexane:EtOAc) to give 4-bromophenyl di-n-butyl phosphate as a clear oil: 32% yield; R$_f$=0.06 (hexane:EtOAc, 4:1); $^1$H NMR (400 MHz, CDCl$_3$) δ 0.93 (t, J=7.4 Hz, 6H, OCH$_2$CH$_2$CH$_2$CH$_3$), 1.35-1.44 (m, 4H, OCH$_2$CH$_2$CH$_2$CH$_3$), 1.63-1.71 (m, 4H, OCH$_2$CH$_2$CH$_2$CH$_3$), 4.08-4.19 (m, 4H, OCH$_2$CH$_2$CH$_2$CH$_3$), 7.09-7.13 (m, 2H, Ar—H), 7.43-7.47 (m, 2H, Ar—H); $^{13}$C NMR (400 MHz, CDCl$_3$) δ 13.49, 13.50, 18.57, 32.13, 32.19, 68.40, 68.46, 117.81, 117.83, 121.74, 121.79, 132.65, 149.86, 149.93.

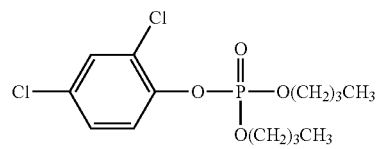

Di-n-butyl 2,4-dichlorophenyl phosphate

Following the representative procedure described above, the crude product was purified by gravity chromatography (silica gel, hexane EtOAc, 9:1) to give di-n-butyl 2,4- dichlorophenyl phosphate as a light yellow oil: 22.26% yield; $R_f$=0.12 (silica gel, hexane: EtOAc, 9:1); $^1$H NMR (400 MHz, CDCl$_3$) δ 0.930 (t, J=7.4 Hz, 6H, OCH$_2$CH$_2$H$_2$CH$_3$)$_2$), 1.36-1.46 (m, 4H, (OCH$_2$CH$_2$CH$_2$CH$_3$)$_2$), 1.65-1.72 (m, 4H, (OCH$_2$CH$_2$CH$_2$CH$_3$)$_2$), 4.14-4.24 (m, 4H, (OCH$_2$CH$_2$CH$_2$CH$_3$)$_2$), 7.26 (dd, 1H, J=8.9, 2.5 Hz, Ph-H), 7.40 (dd, 1H, J=8.8, 1.1 Hz, Ph-H), 7.42 (dd, J=2.6, 1H, 1.1 Hz, Ph-H) $^{13}$C NMR (100 MHz, CDCl$_3$) δ 13.47, 18.54, 32.08, 32.14, 68.73, 68.80, 122.08, 122.10, 126.21, 126.29, 127.92, 130.20, 130.40, 130.42, 145.60, 145.66.

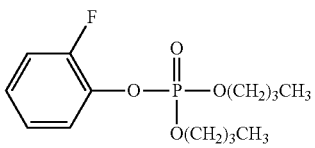

Di-n-butyl 2-fluorophenyl phosphate

Following the representative procedure described above using 2-fluorophenol, the crude product was purified by gravity chromatography (silica gel, hexane:EtOAc, 4:1) to give di-n-butyl 2-fluorophenyl phosphate as a clear oil: 48.25% yield; $R_f$=0.25 (silica gel, hexane:EtOAc, 4:1); $^1$H NMR (400 MHz, CDCl$_3$) δ 0.93 (t, J=7.4 Hz, 6H, (OCH$_2$CH$_2$CH$_2$CH$_3$)$_2$), 1.36-1.46 (m, 4H, (OCH$_2$CH$_2$CH$_2$CH$_3$)$_2$), 1.65-1.72 (m, 4H, (OCH$_2$CH$_2$CH$_2$CH$_3$)$_2$), 4.13-4.24 (m, 4H, (OCH$_2$CH$_2$CH$_2$CH$_3$)$_2$), 7.07-7.17 (m, 3H, Ph-H), 7.35-7.40 (m, 1H, Ph-H); $^{13}$C NMR (100 MHz, CDCl$_3$) δ 13.44, 13.48, 18.52, 32.08, 32.15, 68.47, 68.54, 116.72, 116.91, 122.31, 122.34, 124.40, 124.41, 124.44, 124.45, 125.74, 125.75, 125.80, 125.82, 138.36, 138.42, 138.48, 138.55, 152.24, 152.30, 154.71, 154.77.

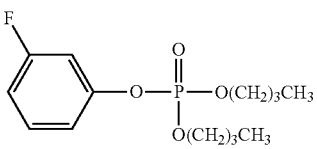

Di-n-butyl 3-fluorophenyl phosphate

Following the representative procedure described above using 3-fluorophenol, the crude product was purified by gravity chromatography (silica gel, hexane:EtOAc, 4:1) to give di-n-butyl 3-fluorophenyl phosphate as a clear oil: 31% yield; $R_f$=0.13 (silica gel, hexane:EtOAc, 4:1); $^1$H NMR (400 MHz, CDCl$_3$) δ 0.93 (t, J=7.4 Hz, 6H, OCH$_2$CH$_2$CH$_2$CH$_3$), 1.36-1.45 (m, 4H, OCH$_2$CH$_2$CH$_2$CH$_3$), 1.64-1.71 (m, 4H, OCH$_2$CH$_2$CH$_2$CH$_3$), 4.10-4.21 (m, 4H, OCH$_2$CH$_2$CH$_2$CH$_3$), 6.87-6.92 (m, 1H, Ar—H), 6.97 (dtd, 1H, J=9.7, 2.3, 0.8 Hz, Ar—H), 7.02-7.04 (m, 1H, Ar—H), 7.29 (td, 1H, 8.2, 6.6 Hz, Ar—H); $^{13}$C NMR (400 MHz, CDCl$_3$) δ 13.48, 18.57, 32.12, 32.19, 68.41, 68.48, 107.94, 107.99, 108.19, 108.24, 111.86, 112.07, 115.68, 115.71, 115.73, 115.76, 130.36, 130.44, 151.50, 151.57, 151.67, 161.76, 164.21.

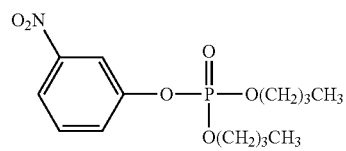

Di-n-butyl 3-nitrophenyl phosphate

Following the representative procedure described above, the crude product was purified by gravity chromatography (silica gel, hexane:EtOAc, 4:1) to give di-n-butyl 3-nitrophenyl phosphate as a light yellow oil: 53% yield; $R_f$=0.18 (silica gel, hexane:EtOAc, 4:1); $^1$H NMR (400 MHz, CDCl$_3$) δ 0.94 (t, J=7.3 Hz, 6H, (OCH$_2$CH$_2$CH$_2$CH$_3$)$_2$), 1.37-1.46 (m, 4H, (OCH$_2$CH$_2$CH$_2$CH$_3$)$_2$), 1.67-1.7 (m, 4H, (OCH$_2$CH$_2$CH$_2$CH$_3$)$_2$), 4.14-4.24 (m, 4H, (OCH$_2$CH$_2$CH$_2$CH$_3$)$_2$), 7.51-7.56 (m, 1H, Ar—H), 7.61 (ddt, 1H, J=8.2, 2.2, 1.1 Hz, Ar—H), 8.05-8.08 (m, 2H, Ph-H); $^{13}$C NMR (100 MHz, CDCl$_3$) δ 13.37, 13.41, 18.49, 32.03, 32.10, 68.67, 68.73, 115.48, 115.53, 119.79, 126.26, 126.31, 130.30, 148.85, 151.10, 151.17.

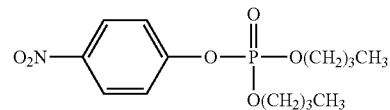

Di-n-butyl 4-nitrophenyl phosphate

Following the representative procedure described above using 4-nitrophenol (1 hour reaction time), the crude product was purified by gravity chromatography (silica gel, hexane: EtOAc, 3:2) to give di-n-butyl 4-nitrophenyl phosphate as a pale yellow oil: 41% yield; $R_f$=0.31 (hexane:EtOAc, 3:2); $^1$H NMR (400 MHz, CDCl$_3$) δ 0.93 (t, J=7.4 Hz, 6H, CH$_2$CH$_2$CH$_2$CH$_3$), 1.36-1.45 (m, 4H, CH$_2$CH$_2$CH$_2$CH$_3$), 1.66-1.73 (m, 4H, CH$_2$CH$_2$CH$_2$CH$_3$), 4.13-4.23 (m, 4H, CH$_2$CH$_2$CH$_2$CH$_3$), 7.36-7.40 (m, 2H, Ar—H), 8.23-8.27 (m, 2H, Ar—H); $^{13}$C NMR (100 MHz, CDCl$_3$) δ 13.46, 18.56, 32.09, 32.16, 68.79, 68.85, 120.47, 120.51, 125.65, 144.60, 155.58, 155.65.

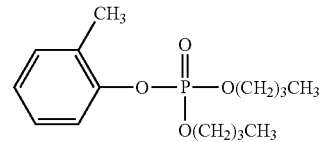

Di-n-butyl 2-methylphenyl phosphate

Following the representative procedure above using 2-methylphenol, the crude product was purified by gravity chromatography (silica gel, 4:1 hexane:EtOAc) to give di-n-butyl 2-methylphenyl phosphate as light yellow oil: 46% yield; $R_f$ (silica gel, 80:20 hexane:EtOAc)=0.18; $^1$H NMR (400 MHz, DCCl$_3$) δ 0.92 (t, J=7.4 Hz, 6H, (OCH$_2$CH$_2$CH$_2$CH$_3$)$_2$), 1.35-1.45 (m, 4H, (OCH$_2$CH$_2$CH$_2$CH$_3$)$_2$), 1.64-1.71 (m, 4H, (OCH$_2$CH$_2$CH$_2$CH$_3$)$_2$), 2.31 (s, 3H, Ar—CH$_3$), 4.09-4.20

(m, 4H, (OCH$_2$CH$_2$CH$_2$CH$_3$)$_2$), 7.04-7.08 (m, 1H, Ar—H), 7.14 (dd, J=7.6, 2.0 Hz, 1H, Ar—H), 7.18-7.20 (m, 1H, Ar—H), 7.27-7.29 (m, 1H, Ar—H); $^{13}$C NMR (100 MHz, CDCl$_3$) δ 13.48, 16.30, 16.31, 18.58, 32.16, 32.24, 68.14, 68.205, 119.64, 119.66, 124.80, 124.82, 126.92, 126.94, 129.14, 129.21, 131.22, 149.21, 149.28. MS m/z 300; Calc. 300.

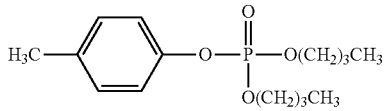

Di-n-butyl 4-methylphenyl phosphate

Following the general procedure above using 4-methylphenol, the crude product was purified by gravity chromatography (silica gel, 4:1 hexane:EtOAc) to give di-n-butyl 4-methylphenyl phosphate as a clear oil:38% yield; R$_f$ (silica gel, 80:20 hexane:EtOAc)=0.20; $^1$H NMR (400 MHz, DCCl$_3$) □□ 0.92 (t, J=7.4 Hz, 6H, (OCH$_2$CH$_2$CH$_2$CH$_3$)$_2$), 1.35-1.44 (m, 4H, (OCH$_2$CH$_2$CH$_2$CH$_3$)$_2$), 1.63-1.70 (m, 4H, (OCH$_2$CH$_2$CH$_2$CH$_3$)$_2$), 2.32 (s, 3H, Ar—CH$_3$), 4.08-4.19 (m, 4H, (OCH$_2$CH$_2$CH$_2$CH$_3$)$_2$), 7.08-7.13 (m, 4H, Ar—H); $^{13}$C NMR (100 MHz, CDCl$_3$) 13.48, 18.57, 20.65, 20.67, 32.14, 32.21, 68.09, 68.15, 119.61, 119.66, 130.04, 134.41, 134.42, 148.54, 148.61. MS m/z 300; Calc. 300.

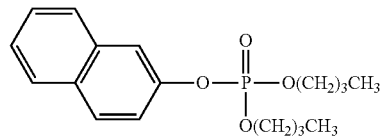

Di-n-butyl 2-naphthyl phosphate

Following the representative procedure described above using 2-naphthol, the crude product was purified by evaporative distillation (b.p. 235° C./0.23 mm Hg) followed by flash column chromatography (silica gel, hexane:EtOAc, 4:1) to give di-n-butyl 2-naphthyl phosphate as a yellow oil: 54.5% yield; Rf=0.30 (hexane:EtOAc, 4:1); $^1$H NMR (400 MHz, CDCl$_3$) δ $^1$H NMR (400 MHz, CDCl3) δ 0.91 (t, J=7.4 Hz, 6H (OCH$_2$CH$_2$CH$_2$CH$_3$)$_2$), 1.36-1.45 (m, 4H (OCH$_2$CH$_2$CH$_2$CH$_3$)$_2$, 1.65-1.72 (m, 4H (OCH$_2$CH$_2$CH$_2$CH$_3$)$_2$), 4.12-4.23 (m, 4H (OCH$_2$CH$_2$CH$_2$CH$_3$)$_2$), 7.36 (dd, J=8.9, 2.4 Hz, 1H, Ar—H), 7.41-7.50 (m, 2H, Ar—H), 7.69 (s, 1H, Ar—H), 7.80 (t, J=9.6 Hz, 3H, Ar—H).

Additional Methods

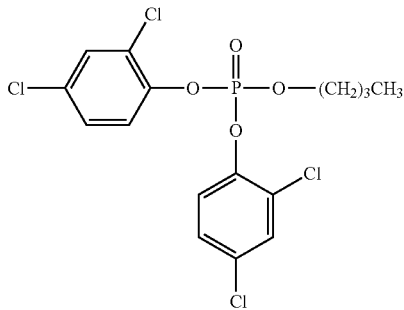

n-Butyl bis(2,4-dichlorophenyl) phosphate

To a round bottom flask charged with pyridine (0.06 mL, 0.00073 mol) in 2 mL dry CH$_2$Cl$_2$ was added n-butyl alcohol (0.067 mL, 0.00073 mol). This solution was added dropwise via cannulation at 0° C. to a solution of bis(2,4dichlorophenyl) phosphorochloridate (0.15 g, 0.00036 mol) in 3 mL dry CH$_2$Cl$_2$. The reaction was allowed to react for 24 hrs at room temperature. The reaction was quenched by extracting with 2 mL 10% HCl, 5 mL saturated NaHCO$_3$ and 10 mL ethyl ether. The aqueous phase was extracted 3×5 mL with diethyl ether. The combined organic layer was dried over MgSO$_4$, filtered and concentrated in vacuo. The crude product was purified by gravity column chromatography (silica gel, EtOAc) to give n-butyl bis(2,4-dichlorophenyl) phosphate as an oil: 10% yield; R$_f$=0.36 (EtOAc); $^1$H NMR (400 MHz, CDCl$_3$) δ 0.93 (t, 3H, J=7.6 Hz, CH$_3$), 1.36-1.46 (m, 2H, CH$_2$CH$_2$CH$_2$CH$_3$), 1.69-1.76 (m, 2H, CH$_2$CH$_2$CH$_2$CH$_3$), 4.37 (q, 2H, J=6.8 Hz, CH$_2$CH$_2$CH$_2$CH$_3$), 7.23 (dd, J=8.8, 2.4 Hz, 1H, Ar—H), 7.40 (dd, 1H, J=8.8, 1.2 Hz, Ar—H), 7.44 (dd, 1H, J=2.8, 1.2 Hz, Ar—H); $^{13}$C NMR (100 MHz, CDCl$_3$) δ 13.44, 18.49, 31.98, 32.05, 70.35, 70.43, 122.23, 122.26, 126.41, 126.48, 128.04, 128.05, 130.42, 131.18, 131.20, 145.14, 145.20.

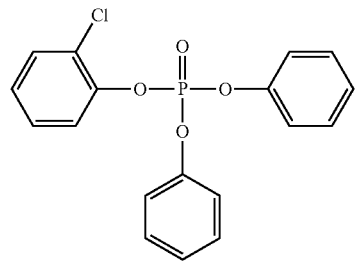 [SMILES: O=P(Oc1ccccc1)(Oc1ccccc1)Oc1ccccc1Cl]

2-Chlorophenyl diphenyl phosphate

To a round bottom flask charged with NaH (0.1662 g of a 60% dispersion in mineral oil, approximately 0.42 mmol) in 3 mL dry THF was added phenol (0.383 g, 0.40 mmol) in 2 mL dry THF. Then this solution was added drop wise via cannulation to a solution of 2-chlorophenyl dichlorophosphate (0.5 g, 0.20 mmol) in 5 mL dry THF at room temperature. The mixture was allowed to react overnight and quenched by adding 10 mL of saturated NaHCO$_3$ and 10 mL of diethyl ether. The aqueous layer was extracted with diethyl ether (3×10 mL). The combined organic layer was dried over MgSO$_4$, filtered and concentrated in vacuo. The crude product was purified by gravity column chromatography (silica gel, hexane:EtOAc, 7:3) to give 2-chlorophenyl diphenyl phosphate as an orange oil: 10% yield; R$_f$=0.22 (silica, hexane:EtOAc, 7:3); $^1$H NMR (400 MHz, CDCl$_3$) δ 7.14 (t, 1H, J=8 Hz, Ar—H), 7.22 (7, 3H, J=7.2 Hz, Ar—H), 7.28 (d, 4H, J=8 Hz, Ar—H), 7.36 (t, 4H, J=8 Hz, Ar—H), 7.41-7.44 (m, 2H, Ar—H); $^{13}$C NMR (100 MHz, CDCl$_3$) δ 120.18, 120.23, 121.36, 121.39, 125.50, 125.58, 125.70, 125.71, 126.31, 127.92, 127.93, 129.83, 130.77, 146.53, 146.59, 150.29, 150.37.

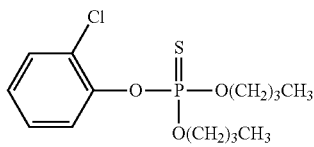

Dibutyl 2-chlorophenyl thiophosphate

A mixture containing n-butanol (0.5 mL, 5.4 mmol) and distilled pyridine (0.45 mL, 5.7 mmol) in 5 mL $CH_2Cl_2$ was added dropwise to 2-chlorophenyl dichlorothiophosphate (0.56 g, 2.1 mmol) dissolved in 15 mL dry $CH_2Cl_2$. The reaction mixture was allowed to stir for 4 days, followed by dilution with 15 mL $CH_2Cl_2$, and extraction with 10% HCl (1×20 mL) and saturated $NaHCO_3$ (3×15 mL). The organic layer was dried under $MgSO_4$, concentrated in vacuo, and purified by evaporative distillation to yield a pale yellow oil; 73% yield: b.p. 145° C./0.1 mmHg; $^1H$ NMR (400 MHz, $CDCl_3$) δ 0.94 (t, J=7.4 Hz, 6H, $CH_2CH_2CH_2CH_3$), 1.39-1.48 (m, 4H, $OCH_2CH_2CH_2CH_3$), 1.68-1.75 (m, 4H, $CH_2CH_2CH_2CH_3$), 4.22 (dt, J=8.8 Hz, 6.5 Hz, 4H, $CH_2CH_2CH_2CH_3$), 7.10-7.14 (m, 1H, Ar—H), 7.22-7.26 (m, 1H, Ar—H), 7.37 (dt, J=8.2 Hz, 1.5 Hz, 1H, Ar—H), 7.42 (dt, J=8.0 Hz, 1.3 Hz, 1H, Ar—H); $^{13}C$ NMR (100 MHz, $CDCl_3$) δ 13.55, 18.70, 31.95, 32.03, 68.93, 69.00, 122.19, 122.22, 125.82, 125.84, 126.11, 126.18, 127.53, 127.54, 130.51, 146.97, 147.04.

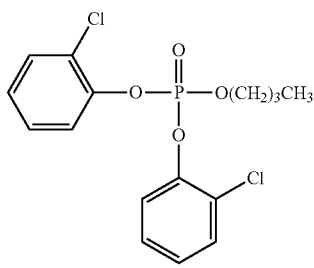

Butyl bis(2-chlorophenyl) phosphate

A mixture containing n-butanol (0.17 mL, 1.86 mmol), and distilled pyridine (0.15 mL, 1.86 mmol) in 5 mL $CH_2Cl_2$ was added dropwise to bis(2-chlorophenyl) chlorophosphate (0.63 g, 1.56 mmol) dissolved in 15 mL dry $CH_2Cl_2$. The reaction mixture was allowed to stir for 24 hours, followed by dilution with 15 mL $CH_2Cl_2$, extraction with 10% HCl (1×20 mL) and saturated $NaHCO_3$ (3×15 mL), and was dried under $MgSO_4$. Upon concentration in vacuo, a pale yellowish oil was obtained in 77% yield: $^1H$ NMR (400 MHz, $CDCl_3$) δ 0.92 (t, J=7.4 Hz, 3H, $CH_2CH_2CH_2CH_3$), 1.37-1.46 (m, 2H, $CH_2CH_2CH_2CH_3$), 1.70-1.77 (m, 2H, $CH_2CH_2CH_2CH_3$), 4.37-4.42 (m, 2H, $CH_2CH_2CH_2CH_3$), 7.11-7.16 (m, 2H, Ar—H), 7.23 (dd, J=8.2 Hz, 1.7 Hz, 2H, Ar—H), 7.42 (dt, J=7.9 Hz, 1.4 Hz, 2H, Ar—H), 7.47 (dt, J=8.2 Hz, 1.4 Hz, 2H, Ar—H); $^{13}C$ NMR (100 MHz, $CDCl_3$) δ 13.45, 18.49, 32.01, 32.07, 69.97, 70.05, 121.49, 121.51, 125.47, 125.55, 126.14, 126.16, 127.87, 127.88, 130.63, 146.50, 146.56.

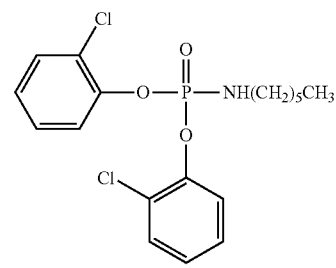

Bis(2-chlorophenyl)N-hexyl phosphoramidate

Into a flame-dried 50 mL round bottom flask was added 2.85 mmol of bis(2-chlorophenyl) chlorophosphate dissolved in 4 mL of $CH_2Cl_2$. This mixture was stirred for fifteen minutes at 0° C. Into a separate flame dried 50 mL round bottom flask was placed 1.6 equivalents of n-hexylamine dissolved in 4 mL of $CH_2Cl_2$ and 1.9 equivalents of pyridine. This solution was allowed to stir for ten minutes at 0° C. The hexylamine/pyridine solution was then added to bis(2-chlorophenyl) chlorophosphate drop wise over a ten minute period via syringe. The reaction was stirred at 0° C. for ten minutes then stirred at room temperature overnight. Reaction mixture was diluted with 16 mL of $CH_2Cl_2$ and washed three times with 20 mL of 10% HCl. The organic layer was washed two times with 18 mL of saturated $NaHCO_3$ solution, dried over $MgSO_4$, and concentrated in vacuo to give bis(2-chlorophenyl)N-hexyl phosphoramidate as a golden oil: 71% yield; $^1H$ NMR (400 MHz, $CDCl_3$) δ 0.85 (t, 3H, J=7.0 Hz, $CH_3$), 1.19-1.28 (m, 6H, $CH_2CH_2CH_2CH_3$), 1.43-1.50 (m, 2H, $NHCH_2CH_2$), 3.1-3.2 (dq, 2H, J=10.8, 7.0 Hz, $NHCH_2$), 3.56 (dt, 1H, J=13.4, 6.7 Hz, NH), 7.07-7.11 (m, 2H, Ar—H), 7.21 (td, 2H, J=7.9, J=1.6, Ar—H), 7.40 (dt, 2H, J=8.0, 1.3 Hz, Ar—H), 7.54 (dt, 2H, J=8.2, 1.3 Hz, Ar—H); $^{13}C$ NMR (100 MHz, $CDCl_3$) δ 13.95, 22.48, 26.06, 31.33, 31.40, 41.87, 121.74, 121.76, 125.45, 125.52, 125.66, 125.67, 127.74, 127.75, 130.46, 146.81, 146.87.

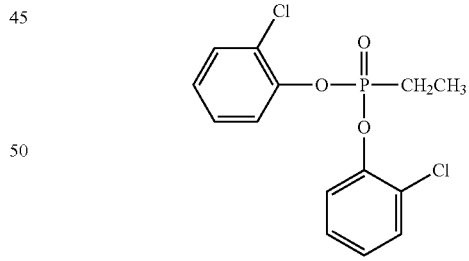

Bis(2-chlorophenyl) ethylphosphonate

A dried round bottom flask was charged with 0.60 mL (0.81 g, 5.5 mmol) of ethyl phosphonic dichloride and 9 mL of dry THF. To another dried round bottom flask sodium hydride (0.558 g of a 60% dispersion in mineral oil, approximately 14 mmol), 7 mL of dry THF and 2.1 equivalents (1.20 mL, 11.6 mmol) of 2-chlorophenol were added. The sodium 2-chlorophenoxide was added to the stirring phosphonic dichloride solution via cannulation. The mixture was allowed to react overnight at room temperature. The reaction mixture was dissolved in 50 mL of diethyl ether and washed three times with 10 mL of saturated sodium bicarbonate. The organic layer was then washed three times with 10 mL of saturated sodium chloride solution, dried over magnesium sulfate, filtered, and concentrated in vacuo to give 2.08 g of a pale yellow oil. The oil was purified by flash column chromatography (silica gel, 3:7, EtOAc:hexane) and evaporatively distilled (220° C./0.2 mm Hg) to afford bis(2-chlorophenyl) ethylphosphonate as a clear colorless oil: 28%; GCMS (m/z) 139 (100%), 295 (M$^+$, 85%); R$_f$=0.41 (2:3, hexane:EtOAc); $^1$H NMR (400 MHz, CDCl$_3$) δ 1.45 (dt, 3H, J=22.0, 7.6 Hz, CH$_2$CH$_3$), 2.26 (dq, 2H, J=18.5, 7.7 Hz, CH$_2$CH$_3$), 7.09-7.14 (m, 1H, Ar—H), 7.17-7.22 (1H, Ar—H), 7.33 (dt, 1H, J=8.2 Hz, 1.5 Hz, Ar—H), 7.42 (ddd, 1H, J=8.0, 1.6, 0.8 Hz, Ar—H); $^{13}$C NMR (100 MHz, CDCl$_3$) δ 19.29, 20.70, 122.26, 122.29, 125.67, 125.73, 125.95, 125.96, 127.81, 127.83, 130.57, 146.22, 146.30.

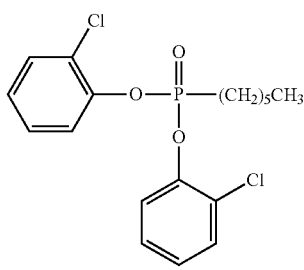

Bis(2-chlorophenyl) hexylphosphonate

Following the procedure above for bis(2-chlorophenyl) ethylphosphonate and using hexyl phosphonic dichloride, the crude product was purified by evaporative distillation (160-185° C./0.25 mm Hg) to remove 2-chlorophenol to afford bis(2-chlorophenyl) hexylphosphonate as a clear colorless oil: 50% yield; $^1$H NMR (400 MHz, CDCl$_3$) δ 0.88-0.91 m, 3H, CH$_3$), 1.30-1.35 (m, 4H, (CH$_2$)$_3$(CH$_2$)$_2$CH$_3$), 1.44-1.52 (m, 2H, (CH$_2$)$_2$CH$_2$(CH$_2$)$_2$CH$_3$), 1.84-1.95 (m, 2H, CH$_2$CH$_2$(CH$_2$)$_3$CH$_3$), 2.18-2.27 (m, 2H, CH$_2$(CH$_2$)$_4$CH$_3$), 7.09-7.13 (m, 1H, Ar—H), 7.19 (td, 1H, J=8.0, 1.7 Hz, Ar—H), 7.33 (dt, 1H, J=8.2, 1.5 Hz, Ar—H), 7.40-7.43 (m, 1H, Ar—H).

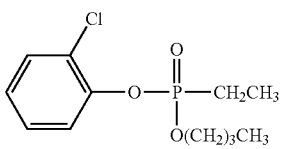

Butyl 2-chlorophenyl ethylphosphonate

To a dried round bottom flask 0.420 g (1.27 mmol) of bis(2-chlorophenyl) ethylphosphonate in 10 mL of dry THF with stirring was added. To another dried round bottom flask sodium hydride (0.0645 g of a 60% dispersion in mineral oil, approximately 1.6 mmol) and 3 mL of dry THF were added, followed by 1.1 equivalents (0.125 mL, 1.37 mmol) of anhydrous 1-butanol. The sodium butoxide was added to the stirring phosphonate solution via cannulation. After allowing the mixture to react for 36 hours at room temperature, an additional 0.32 equivalents of sodium butoxide was added to the reaction mixture via syringe. The reaction mixture was allowed to react overnight at room temperature. The reaction mixture was diluted in 50 mL of diethyl ether and washed three times with 10 mL of saturated sodium bicarbonate solution. The organic layer was then washed three times with 10 mL of saturated sodium chloride solution, dried over magnesium sulfate, filtered, and concentrated in vacuo to give 0.09 g of a yellow oil. The crude product was purified by gravity column chromatography (gravity grade silica gel, 3:2, EtOAc:hexane) to afford butyl 2-chlorophenyl ethylphosphonate as a clear colorless oil: 2% yield, GCMS (m/z) 185 (100%), 276 (M$^+$, 1%); $^1$H NMR (400 MHz, CDCl$_3$) δ 0.91 (t, 3H, J=7.2 Hz, OCH$_2$CH$_2$CH$_2$CH$_3$), 1.24-1.43 (m, 5H, OCH$_2$CH$_2$CH$_2$CH$_3$ and PCH$_2$CH$_3$), 1.60-1.69 (m, 2H, OCH$_2$CH$_2$CH$_2$CH$_3$), 1.94-2.04 (m, 2H, PCH$_2$CH$_3$), 4.06-4.24 (m, 2H, OCH$_2$(CH$_2$)$_2$CH$_3$), 7.10 (t, 1H, 5 Hz, Ar—H), 7.21-7.26 (m, 1H, Ar—H), 7.40 (dd, 1H, J=7.9, 1.4 Hz, Ar—H), 7.46 (d, 1H, J=12.8 Hz, Ar—H).

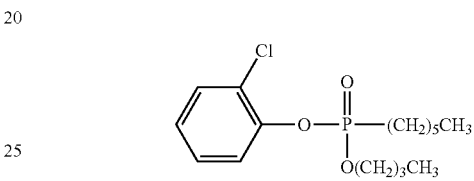

Butyl 2-chlorophenyl hexylphosphonate

Following the procedure above for butyl 2-chlorophenyl ethylphosphonate and using bis(2-chlorophenyl) hexylphosphonate, the crude product was purified by evaporative distillation to remove 2-chlorophenol (140-165° C./0.18 mm Hg) to afford butyl 2-chlorophenyl hexylphosphonate as an oil: 6% yield; $^1$H NMR (400 MHz, CDCl$_3$) δ 0.89 (t, 3H, J=6.9 Hz, CH$_3$), 0.91 (t, 3H, J=7.4 Hz, CH$_3$), 1.27-1.45 (m, 8H, OCH$_2$CH$_2$CH$_2$CH$_3$, (CH$_2$)$_2$(CH$_2$)$_3$CH$_3$), 1.60-1.77 (m, 4H, OCH$_2$CH$_2$CH$_2$CH$_3$, CH$_2$CH$_2$(CH$_2$)$_3$CH$_3$), 1.92-2.00 (m, 2H, CH$_2$(CH$_2$)$_4$CH$_3$), 4.05-4.21 (m, 2H, OCH$_2$CH$_2$CH$_2$CH$_3$), 7.07-7.11 (m, 1H, Ar—H), 7.23 (td, 1H, J=8.0, 1.6 Hz, Ar—H), 7.39-7.41 (m, 1H, Ar—H), 7.45 (dt, 1H, J=8.2, 1.4 Hz, Ar—H).

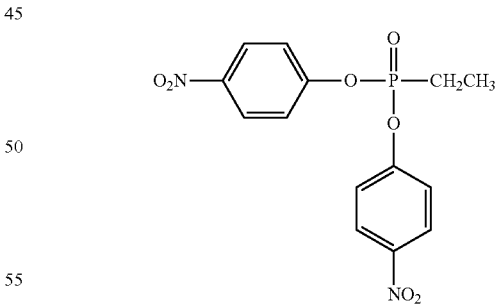

Bis (p-nitrophenyl) ethylphosphonate

To a round bottom flask charged with NaH (0.333 g, 0.0138 mol) in 5 mL dry THF was added 4-nitrophenol (1.1359 g, 0.0081 mol) in 5 mL dry THF. A solution of ethyl phosphonic dichloride (0.6 g, 0.0040 mol) in 5 mL dry THF was then added via cannulation at room temperature. The reaction was allowed to react overnight. The reaction was quenched by adding 15 mL of CH$_2$Cl$_2$ and 15 mL of saturated NaHCO₃. The aqueous layer was extracted with methylene chloride 3×20 mL. The combined organic layer was dried over MgSO₄, filtered and concentrated in vacuo. The crude solid product was dissolved in CH₂Cl₂ and the organic layer extracted several times with saturated NaHCO₃. The organic layer was dried over MgSO₄, filtered and concentrated in vacuo to give bis(p-nitrophenyl) ethylphosphonate as a white solid (mp 157-159° C.): 15% yield; ¹H NMR (400 MHz, CDCl₃) δ 1.40 (dt, 3H, J=22.4, 7.6 Hz. CH₃), 2.22 (dq, CH₂, J=18.4, 7.6 Hz, CH₂), 7.36-7.39 (m, 2H, Ar—H), 8.23-8.26 (m, 2H, Ar—H); ¹³C NMR (100 MHz, CDCl₃) δ 6.30, 6.38, 19.01, 20.42, 120.97, 121.02, 125.83, 144.98, 154.75, 154.84.

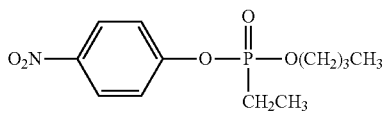

Butyl p-nitrophenyl ethylphosphonate

To a round bottom flask with NaH (0.007 g of a 60% dispersion in mineral oil, approximately 0.18 mmol) in 1 mL dry THF was added dry 1-butanol (0.016 mL, 0.18 mmol). This solution was added drop wise via cannulation to a solution of bis(p-nitrophenyl) ethylphosphonate (0.093 mg, 0.26 mmol) in 3 mL dry THF in an ice/water bath. The mixture was allowed to react at room temperature overnight. The reaction was quenched by adding 5 mL of methylene chloride and 5 mL of NaHCO₃. The aqueous layer was extracted with methylene chloride (3×5 mL). The organic layer was combined and dried over MgSO₄, filtered and concentrated in vacuo. The crude product was purified by gravity column chromatography (silica gel, 70:30, EtOAc:hexane) to give butyl p-nitrophenyl ethylphosphonate as an oil: 26% yield; Rf=0.3 (silica gel, 70:30, EtOAc:hexane); ¹H NMR (400 MHz, CDCl₃) δ 0.92 (t, J=7.4 Hz, 3H, OCH₂CH₂CH₂CH₃), 1.27 (dt, J=21.1, 7.7 Hz, 3H, PCH₂CH₃), 1.34-1.42 (m, 2H, OCH₂CH₂CH₂CH₃), 1.61-1.68 (m, 2H, OCH₂CH₂CH₂CH₃), 1.96 (dq, J=18.3, 7.6 Hz, 2H, PCH₂CH₃), 4.08 (dq, J=10.1, 6.6 Hz, 1H, OCH(H)CH₂CH₂CH₃), 4.14-4.22 (m, 1H, OCH(H)CH₂CH₂CH₃), 7.39 (dd, J=9.3, 1.1 Hz, 2H, Ar—H), 8.24 (d, J=8.9 Hz, 2H, Ar—H).

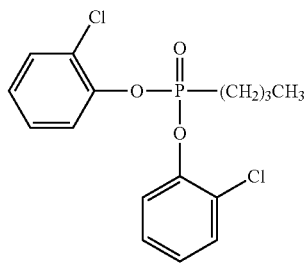

Bis(2-chlorophenyl) n-butylphosphonate

Into a dried three-neck 100 mL round bottom flask equipped with an addition funnel and a reflux condenser were added magnesium turnings (4.0 g/17 mmol) followed by 1 mL of dry diethyl ether. To this mixture was added drop wise with stirring at room temperature a solution of 1-bromobutane (1.8 mL/17 mmol) in 4 mL of diethyl ether over 30 minutes. After Grignard reagent formation was complete, 2-chlorophenyl dichlorophosphate (1.23 g/5.0 mmol) in 2 mL diethyl ether was added drop wise at rt. After allowing the mixture to stir for 2.5 h, it was worked up by addition of saturated aqueous NH₄Cl and the organic layer separated. The aqueous layer was extracted with diethyl ether (3×) and the combined organic layer extracted with brine, dried over MgSO₄, filtered and concentrated in vacuo. The yellowish oil was purified by flash chromatography (silica gel, 3:2, hexane: EtOAc) to give bis(2-chlorophenyl) butylphosphinate as an oil: 21% yield; Rf=0.35 (3:2, hexane:EtOAc); ¹H NMR (400 MHz, CDCl₃) δ 0.96 (t, 3H, J=7.4 Hz, CH₂CH₂CH₂CH₃), 1.51 (sextet, 2H, J=7.4 Hz, CH₂CH₂CH₂CH₃), 1.84-1.95 (m, 2H, CH₂CH₂CH₂CH₃), 2.19-2.28 (m, 2H, CH₂CH₂CH₂CH₃), 7.08-7.13 (m, 1H, Ar—H), 7.19 (td, 1H, J=8.0, 1.7 Hz, Ar—H), 7.33 (dt, 1H, J=8.2, 1.4 Hz, Ar—H), 7.41 (ddd, 1H, J=7.9, 1.6. 0.8 Hz, Ar—H); ¹³C NMR (100 MHz, CDCl₃) δ 16.46, 16.64, 17.16, 17.21, 18.55, 19.94115.25, 115.28, 118.63, 118.69, 118.90, 118.92, 120.79, 120.80, 123.54, 139.24, 139.32.

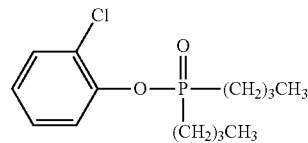

2-Chlorophenyl di-n-butylphosphinate

The title compound was also isolated during the chromatographic purification of bis(2-chlorophenyl) n-butylphosphonate. Therefore, the 2-chlorophenyl di-n-butylphosphinate was further purified by flash chromatography (silica gel, 4:1 to 3:2, hexane: EtOAc) to give the title compound as an oil: 9% yield; Rf=0.23 (3:2, hexane:EtOAc); 0.92 (t, 6H, J=7.2 Hz, CH₂CH₂CH₂CH₃), 1.42 (sextet, 4H, J=7.4 Hz, CH₂CH₂CH₂CH₃), 1.54-1.75 (m, 4H, CH₂CH₂CH₂CH₃), 1.84-1.96 (m, 4H, CH₂CH₂CH₂CH₃), 7.06-7.10 (m, 1H, Ar—H), 7.22 (td, 1H, J=7.9, 1.7 Hz, Ar—H), 7.39 (dd, 1H, J=8.0, 1.6 Hz, Ar—H), 7.54 (dt, 1H, J=8.2, 1.4 Hz, Ar—H).

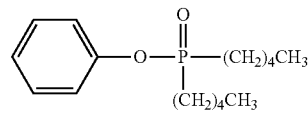

Phenyl di-n-pentylphosphinate

Into a dried three-neck 100 mL round bottom flask was added 1.5 equivalents of magnesium turnings and 4 mL of dry THF. This mixture was stirred at room temperature. To a second dried round bottom flask was added 1.5 equivalents of 1-bromopentane diluted in 4 mL of THF. This mixture was stirred for five minutes and transferred to an addition funnel. The 1-bromopentane was added to the magnesium turnings drop wise over a thirty minute period at room temperature. The Grignard reagent begin to form fifteen minutes after the addition was completed. To a third dried round bottom flask was added phenyl dichlorophosphate dissolved in 1 mL of THF and transferred to the addition funnel. The phenyl dichlorophosphate/THF was added to the 1-bromopentane mixture over a fifteen minute period at 0° C. The reaction mixture was stirred at 0° C. for 35 minutes and then removed from the ice bath and allowed to continue stirring for 1.5 hours at room temperature. A golden liquid was obtained and was worked up using saturated NH$_4$Cl. The organic layer was isolated and washed with brine and dried over MgSO$_4$, filtered, concentrated in vacuo and purified by flash chromatography (silica gel, 3:2, hexane: EtOAc) to give phenyl di-n-pentylphosphinate as a golden oil: 3% yield; R$_f$=0.33 (silica, 3:2, hexane: EtOAc); $^1$H NMR (400 MHz, CDCl$_3$) δ 0.8 (t, J=7.2 Hz, 6H, (CH$_2$CH$_2$CH$_2$CH$_2$CH$_3$)$_2$), 1.29-1.39 (m, 8H, CH$_2$CH$_2$CH$_2$CH$_2$), 1.61-1.68 (m, 4H, PCH$_2$CH$_2$), 1.79-1.88 (m, 4H, PCH$_2$CH$_2$), 7.12-7.34 (m, 5H, Ph-H); $^{13}$C NMR (100 MHz, CDCl$_3$) δ 13.76, 13.78, 21.53, 21.56, 22.11, 32.84, 32.99, 95.33, 96.08, 120.62, 120.67, 124.57, 129.50, 129.64, 129.75.

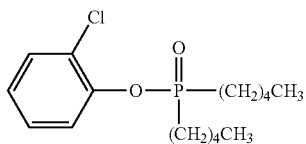

2-Chlorophenyl di-n-pentylphosphinate

Following the procedure above for the synthesis of phenyl dipentylphosphinate using 2-chlorophenyl dichlorophosphate, the crude product was purified by flash chromatography (silica gel, 3:2, hexane: EtOAc) to give 2-chlorophenyl di-n-pentylphosphinate as a golden oil: 11% yield; R$_f$=0.33 (silica, 3:2, hexane:EtOAc); $^1$H NMR (400 MHz, CDCl$_3$) δ 0.89 (t, J=7.6 Hz, 6H, (CH$_2$CH$_2$CH$_2$CH$_2$CH$_3$)$_2$), 1.28-1.41 (m, 8H, CH$_2$CH$_2$CH$_2$CH$_2$), 1.60-1.73 (m, 4H, PCH$_2$CH$_2$), 1.86-1.93 (m, 4H, PCH$_2$CH$_2$), 7.08 (t, J=7.7 Hz, 1H, Ar—H), 7.19-7.23 (m, 1H, Ar—H), 7.39 (d, J=7.9 Hz, 1H, Ar—H), 7.55 (dd, J=8.1, 1.0 Hz, 1H, Ar—H).

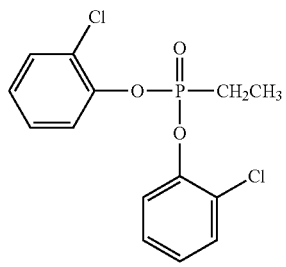 [SMILES: CCP(=O)(Oc1ccccc1Cl)Oc1ccccc1Cl]

Bis(2-chlorophenyl) ethylphosphonate

A dried round bottom flask was charged with 0.60 mL (0.81 g, 5.5 mmol) of ethyl phosphonic dichloride and 9 mL of dry THF. To another dried round bottom flask sodium hydride (0.558 g of a 60% dispersion in mineral oil, approximately 14 mmol), 7 mL of dry THF and 2.1 equivalents (1.20 mL, 11.6 mmol) of 2-chlorophenol were added. The sodium 2-chlorophenoxide was added to the stirring phosphonic dichloride solution via cannulation. The mixture was allowed to react overnight at room temperature. The reaction mixture was dissolved in 50 mL of diethyl ether and washed three times with 10 mL of saturated sodium bicarbonate. The organic layer was then washed three times with 10 mL of saturated sodium chloride solution, dried over magnesium sulfate, filtered, and concentrated in vacuo to give 2.08 g of a pale yellow oil. The oil was purified by flash column chromatography (silica gel, 3:7, EtOAc:hexane) and evaporatively distilled (220° C./0.2 mm Hg) to afford bis(2-chlorophenyl) ethylphosphonate as a clear colorless oil: 28%; GCMS (m/z) 139 (100%), 295 (M$^+$, 85%); R$_f$=0.41 (2:3, hexane:EtOAc); $^1$H NMR (400 MHz, CDCl$_3$) δ 1.45 (dt, 3H, J=22.0, 7.6 Hz, CH$_2$CH$_3$), 2.26 (dq, 2H, J=18.5, 7.7 Hz, CH$_2$CH$_3$), 7.09-7.14 (m, 1H, Ar—H), 7.17-7.22 (1H, Ar—H), 7.33 (dt, 1H, J=8.2 Hz, 1.5 Hz, Ar—H), 7.42 (ddd, 1H, J=8.0, 1.6, 0.8 Hz, Ar—H); $^{13}$C NMR (100 MHz, CDCl$_3$) δ 19.29, 20.70, 122.26, 122.29, 125.67, 125.73, 125.95, 125.96, 127.81, 127.83, 130.57, 146.22, 146.30.

Example 2: Cholinesterase Assays

Acetylcholinesterase (from electric eel), butyrylcholinesterase (from horse serum), DTNB, butyrylthiocholine, acetylthiocholine, and BSA were purchased from Sigma. The dialkyl 2-chlorophenyl (and 4-chlorophenyl) phosphates were solubilized in reagent grade methanol.

Cholinesterase activity measurements were performed essentially according to the method of Ellman (Biochemical Pharmacology 7:88-90, 1961). The composition of the assay mixture was 0.1 M sodium phosphate, pH 7.5, 0.033 M DTNB, 0.001 M MgCl$_2$, and 100 μg/mL of BSA containing appropriate amounts of substrate and inhibitor. Each assay was initiated by the addition of substrate and the activity quantified by measuring the formation of the thionitrobenzoate anion at 412 nm at 37° C. Methanol used to solubilize the dialkyl phenyl phosphates [1% (v/v) final concentration] had no inhibitory effect on either enzyme.

Butyrylcholinesterase was pre-incubated at room temperature with inhibitor in the assay cocktail minus substrate for varying periods of time at 25° C. Substrate was then added and the activity measured as described above. The relative rates of enzyme inactivation were determined by plotting enzyme activity versus time of pre-incubation with inhibitor. Results were expressed as the rate constant for the rate of enzyme inactivation. In the case of AcChase, results were expressed as the % of activity remaining relative to the enzyme incubated only with solvents.

Enzyme activity was also measured by native gel electrophoresis. For cholinesterase activity, proteins (10 μg of both acetylcholinesterase and butyrylcholinesterase) were fractionated on Novex precast 10% Tris glycine gels (Invitrogen). Enzyme activity was detected by first incubating the gels in a solution of 5 mM substrate then staining with a solution of copper sulfate/potassium ferricyanide.

The first series of experiments determined the effect of the dialkyl 2-chlorophenyl (and 4-chlorophenyl) phosphates on both AcChase and BuChase. None of the compounds had any inhibitory effect on AcChase (See Table 1). In Table 1, AcChase was incubated with 100 μM of the indicated phenyl phosphate for 60 minutes at 25° C. and then assayed as described above. Results were expressed as the % activity relative to enzyme incubated with solvent ±SD (standard deviation).

TABLE 1

Effect of dialkyl 2-chlorophenyl phosphates on acetylcholinesterase activity.

| Compound | % Activity ± SD |
|---|---|
| Di-methyl- | 101.9 ± 0.019 |
| Di-ethyl- | 96.77 ± 0.019 |
| Di-n-propyl- | 97.38 ± 0.028 |
| Di-iso-propyl- | 97.82 ± 0.045 |
| Di-n-butyl- | 97.60 ± 0.029 |
| Di-iso-butyl- | 96.18 ± 0.023 |
| Di-n-butyl-(4Cl) | 97.61 ± 0.006 |
| Di-n-pentyl- | 101.7 ± 0.030 |

In contrast, several of the compounds showed inhibitory activity on BuChase. While di-methyl- and di-isopropyl 2-chlorophenyl phosphates appeared to have no effect on BuChase activity under standard conditions, they showed inhibitory activity when their concentration was increase as shown in Table 2. The remaining derivatives showed significant inhibitory activity against the enzyme under standard conditions (Table 2). Interestingly, the degree of inhibitory activity, measured as the rate of enzyme inactivation, appears to be a function of the structure of the derivative. In Table 2, BuChase was incubated for increasing periods of time at 25° C. with 100 nM inhibitor then assayed for activity as described above. Rate constants were calculated from a plot of enzyme activity vs. time of inhibitor exposure. Activity measurements at each time point (3 to 4 per compound) were performed in triplicate. Slopes were calculated by linear regression analysis.

TABLE 2

Rates of inactivation of butyrylcholinesterase by di-alkyl 2-chlorophenyl phosphates.

| Compound: (di-alkyl 2-chlorophenyl phosphate) | $k$ (min$^{-1}$) × 10$^{-2}$ ± S.E.M/Comments |
|---|---|
| Di-methyl- | Inhibitory at 10$^{-4}$M, 48.9% Inhibition |
| Di-isopropyl- | Inhibitory at 10$^{-4}$M, 85.3% Inhibition |
| Di-ethyl- | 6.64 ± 2.1 |
| Di-n-prop- | 20.21 ± 2.2 |
| Di-n-butyl- | 64.76 ± 3.0 |
| Di-isobutyl- | 60.83 ± 5.8 |
| Di-n-butyl-(4Cl) | 13.01 ± 2.0 |
| Di-n-pentyl- | 30.44 ± 3.3 |
| Control | 1.64 ± 1.1 |

Exhaustive dialysis of the inhibited enzyme did not restore enzyme activity, suggesting that the enzyme had been covalently modified, i.e., phosphorylation of the serine within the enzyme's catalytic triad. In some cases of inhibition, cholinesterases are capable of regaining catalytic activity.

Table 3 depicts reactivation of inactive butyrylcholinesterase. BuChase was incubated with excess di-butyl 2-chlorophenyl phosphate for 60 min at 4° C. The excess phosphate was removed using a desalting column. The inactivated BuChase was incubated at 4° C. for various periods of time and then assayed for activity. Results were expressed as percent inhibition and calculated using the following formula; [(activity with solvent only)—(activity with DB-2Cl-PP)]/(activity with solvent only)×100%. There is no significant reactivation over 24 hours as the % remaining activities are statistically the same.

TABLE 3

Reactivation of inactive butyrylcholinesterase

| | Incubation Period | | | |
|---|---|---|---|---|
| | 0 hours | 3.5 hours | 7 hours | 24 hours |
| % Remaining Activity | 0.6 | 0.6 | 0.8 | 1.1 |

Using native gel electrophoresis, both AcChase and BuChase activity was detected. Pre-incubation of AcChase with di-ethyl 2-chlorophenyl phosphate had no effect on AcChase activity (FIG. 1). In contrast, the activity of BuChase was nearly completely inhibited by di-ethyl 2-chlorophenyl phosphate (FIG. 2A).

The cholinesterases were pre-incubated with $^{14}$C-di-ethyl-2-chlorophenyl phosphate and then fractionated by native gel electrophoresis as described above. The proteins were fixed in the gel with 10% acetic acid/30% methanol. The fixative was removed and replaced with 100 mL of EN$^3$HANCE. The gel was incubated for 60 minutes at room temperature with gentle agitation and then placed in 5% PEG and incubated for 30 minutes at room temperature with gentle agitation. The gel was then dried down on a piece of 3 MM filter paper, exposed to X-ray film at −80° C. for 2 weeks, and then developed. Pre-incubation of BuChase with $^{14}$C-labeled di-ethyl 2-chlorophenyl phosphate and gel electrophoresis of the mixture showed that the compound had been covalently modified by the compound (FIG. 2B).

Table 4 below shows the relative inhibitory activity of exemplary compounds of the present disclosure. The results were obtained by pre-incubating the enzyme with the compound (final concentration 10$^{-7}$M) for various periods of time and measuring the remaining enzyme activity. The results are shown as the change in absorbance at 412 nm/minute. In order to simplify the results from all the compounds, the enzyme activities were normalized to 2-chlorophenyl-di-n-butyl phosphate which was set as 1.0. Since two different preparations of enzyme were used, the normalization procedure would adjust for any differences in the amount of enzyme. Several of the compounds are potent inhibitors, i.e., the rates of inactivation are so fast that they were not measurable under these conditions. In other cases, the compound's inhibitory activity is not as strong and assay conditions were modified to increase the inhibitor concentration.

Table 4: Rates of inactivation of butyrylcholinesterase by exemplary compounds: Change in Absorbance at 412 nm/Minute. (ND=No Data)

TABLE 4
| Compounds | Change in Absorbance at 412 nm/Minute (Not Normalized)/ Comments | Change in Absorbance at 412 nm/Minute (Normalized) |
|---|---|---|
| 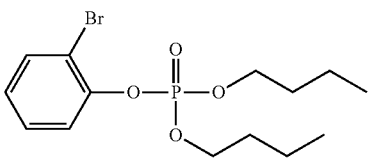<br>"2-bromo" | 0.918 | 1.366 |
| 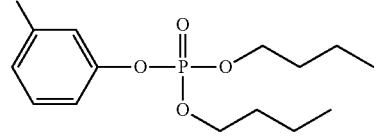<br>"3-bromo" | 4.18 | 6.220 |
| 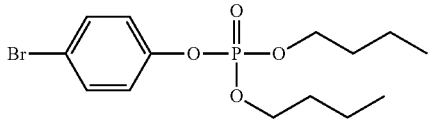<br>"4-bromo" | 0.495 | 0.737 |
| 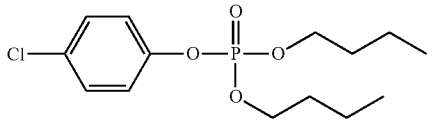<br>"4-chloro" | 0.227 | 0.338 |
| 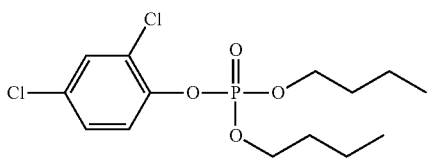<br>"2,4-dichloro" | 92% inhibition after 1 minute under standard conditions | |
| 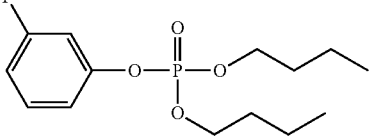<br>"3-fluoro" | 0.468 | 0.696 |
| 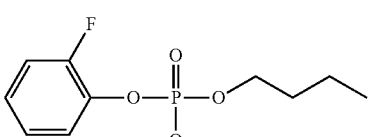<br>"2-fluoro" | 1.75 | 2.604 |

TABLE 4-continued

| Compounds | Change in Absorbance at 412 nm/Minute (Not Normalized)/ Comments | Change in Absorbance at 412 nm/Minute (Normalized) |
|---|---|---|
| 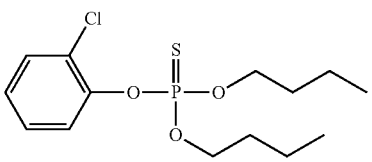<br>"thio" | Not Inhibitory under standard conditions/ Inhibitory at $10^{-4}$ M. 14.6% inhibition | |
| 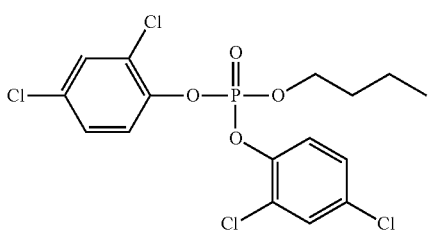<br>"bis(2,4-dichlorophenyl)" | Not inhibitory under standard conditions. Inhibitory at $10^{-4}$ M: 63.4% inhibition. | |
| 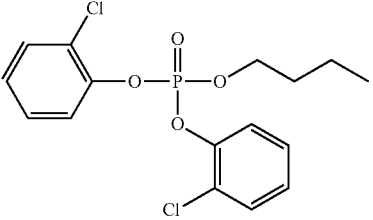<br>"bis(2-chlorophenyl)" | ND | ND |
| 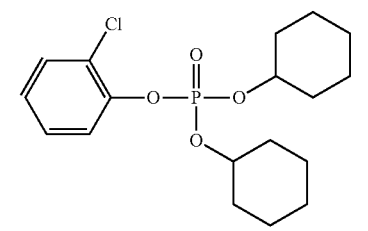<br>"2-chlorophenyl dicyclohexyl" | ND | ND |
| 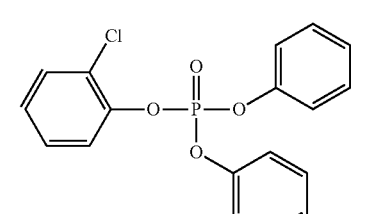<br>"2-chlorophenyl diphenyl" | Not inhibitory under standard conditions. Inhibitory a $10^{-4}$ M: 29.4% inhibition | |
| 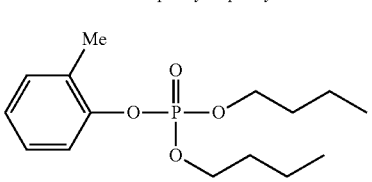<br>"2-methyl" | Reversible inhibitor: $K_i = 2.1$ μM | |

TABLE 4-continued
| Compounds | Change in Absorbance at 412 nm/Minute (Not Normalized)/ Comments | Change in Absorbance at 412 nm/Minute (Normalized) |
|---|---|---|
| 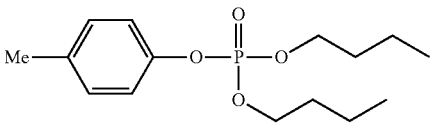 "4-methyl" | ND | ND |
| 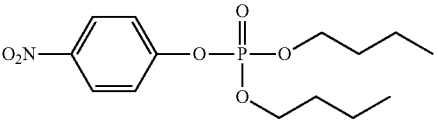 "4-nitro" | 100% Inhibition (Immediate under standard conditions) | |
| 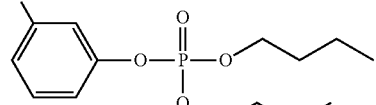 "4-nitro" | 83% Inhibition (Immediate). 100% Inhibition after 2 minutes | |
| 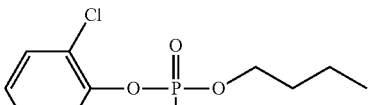 "2-Cl-phenyl hexyl" | 10.04 | 14.94 |
| 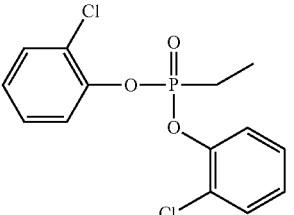 "bis 2Cl-phenyl" | 0.688 | 1.024 |
| 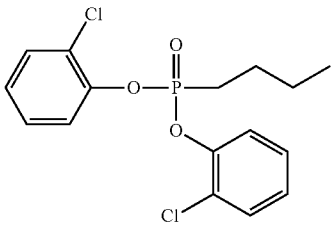 [SMILES: CCCCP(=O)(Oc1ccccc1Cl)Oc1ccccc1Cl] | 0.32 | 0.48 |
| 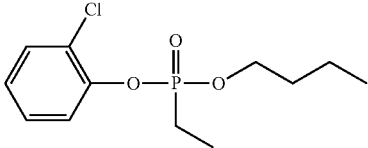 "2-Cl-phenyl ethyl" | ND | ND |

TABLE 4-continued
| Compounds | Change in Absorbance at 412 nm/Minute (Not Normalized)/ Comments | Change in Absorbance at 412 nm/Minute (Normalized) |
|---|---|---|
| 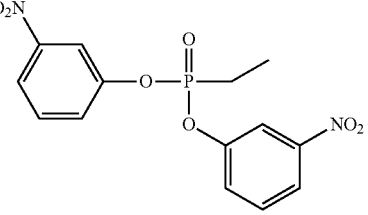 "bis m-nitrophenyl" | ND | ND |
| 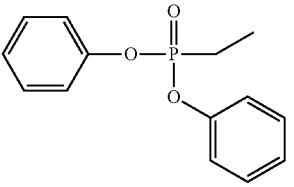 "bis phenyl" | ND | ND |
| 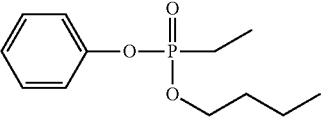 "bis phenyl butyl ethyl" | ND | ND |
| 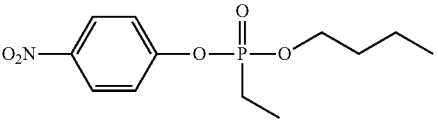 "4-nitrophenyl O-butyl ethyl" | 100% inhibition under standard conditions | ND |
| 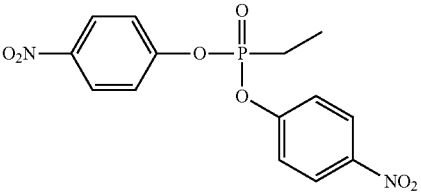 "bis p-nitrophenyl" | ND | ND |
| 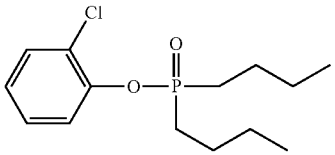 "2-chlorophenyl dibutyl" | 0.684 | 1.018 |
| 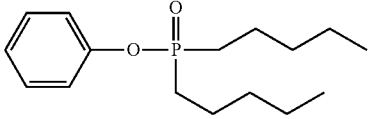 "phenyl dipentyl" | ND | ND |

TABLE 4-continued

| Compounds | Change in Absorbance at 412 nm/Minute (Not Normalized)/ Comments | Change in Absorbance at 412 nm/Minute (Normalized) |
|---|---|---|
| 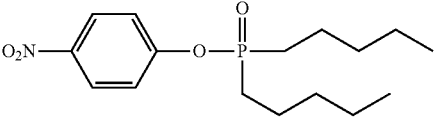 "4-nitrophenyl dipentyl" | ND | ND |
| 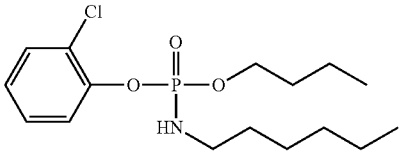 "2-Cl-phenyl N-hexyl" | 0.688 | 1.024 |
| 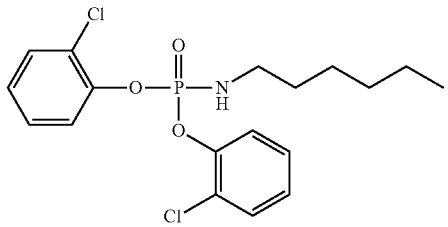 "bis-(2-Cl-phenyl) N-hexyl" | Not inhibitory under standard conditions. Inhibitory a $10^{-4}$ M: 73.9% inhibition. | |

Figure 12:
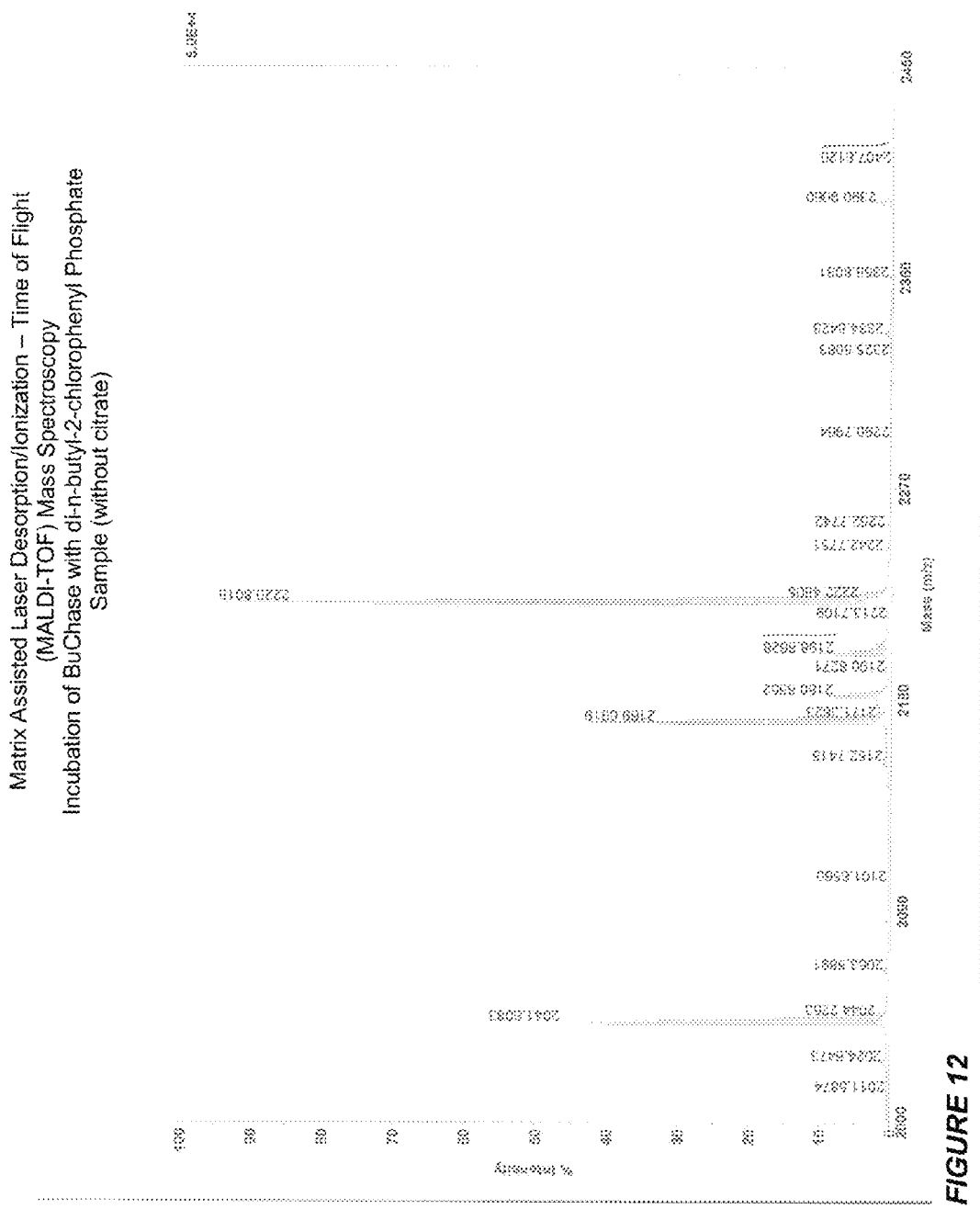
FIG. 12 shows a spectrum resulting from Matrix Assisted Laser Desorption/Ionization Time of Flight (MALDI-TOF) Mass Spectroscopy. BuChase was incubated with di-n-butyl-2-chlorophenyl phosphate. The excess inhibitor was removed and BuChase was digested with trypsin. The tryptic peptides were then analyzed by MALDI-TOF.

Matrix Assisted Laser Desorption/Ionization Time of Flight (MALDI-TOF) Mass Spectroscopy was used to show that BuChase was covalently modified (FIG. 12). BuChase was incubated with di-n-butyl-2-chlorophenyl phosphate. Excess inhibitor was removed and the enzyme was digested with trypsin. The tryptic peptides were then analyzed by MALDI-TOF. Unmodified peptide containing the active site serine (MW 2198.86) and modified peptide (MW 2390.9060) can be seen. This is what would be predicted if BuChase had been covalently modified. Irreversible inhibitors usually covalently modify an enzyme, and inhibition cannot therefore be reversed. This results shows that di-n-butyl-2-chlorophenyl phosphate is likely an irreversible inhibitor.

Many of the presently disclosed compounds are irreversible inhibitors. In some respects, it may be desirable to have irreversible inhibitors which act on butyrylcholinesterase as there may be such advantages as reduced dosage and greater efficacy, etc.

Example 3: Specificity of Butyrylcholinesterase Inhibitors

The specificity of di-n-butyl 2-chlorophenyl phosphate (DB-2Cl-PP) was determined by its effects on the serine proteases trypsin and chymotrypsin, protein kinases Protein Kinase A and S6K2, and hexokinase.

Figure 5:
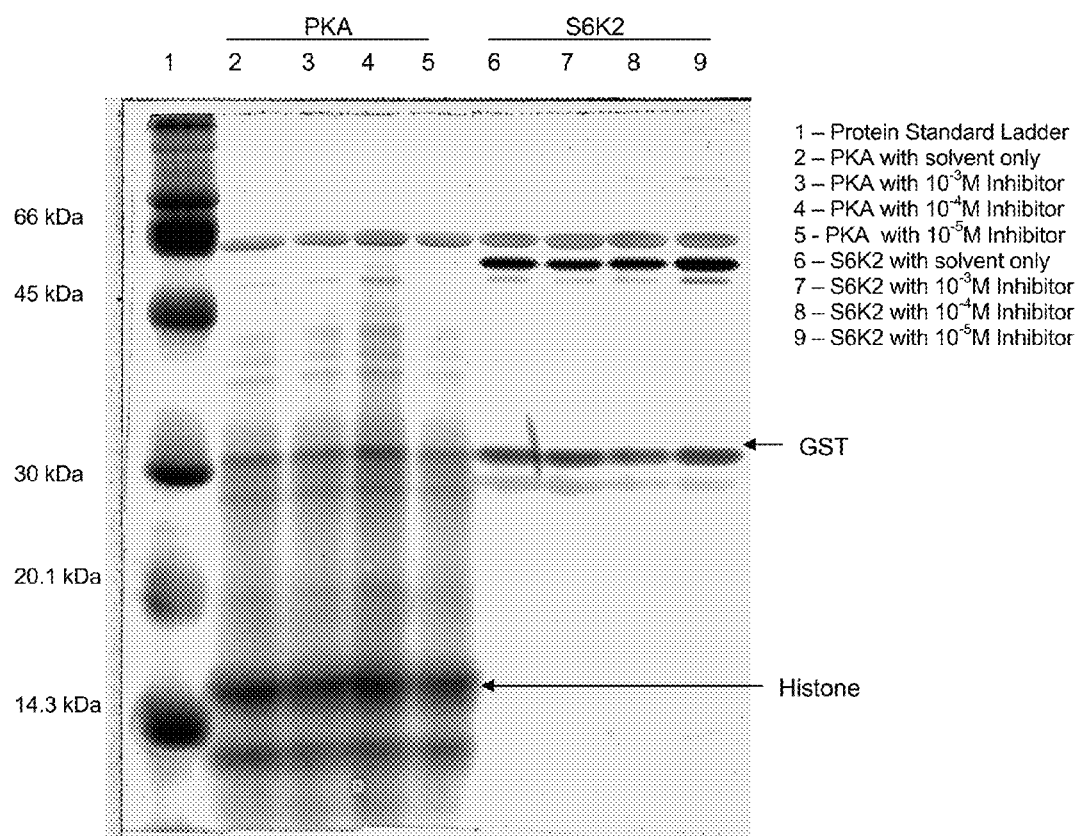
FIG. 5 depicts the effect of di-n-butyl 2-chlorophenyl phosphate on the activity of PKA and S6K2. Protein Kinase A (PKA) and S6K2 were incubated with the indicated concentrations of di-n-butyl 2-chlorophenyl phosphate and assayed as described previously. The reaction mixtures were separated by SDS-PAGE, and then stained for phosphoproteins with Pro-Q® Diamond.

For protein kinase activity, histone was used as the substrate for protein kinase A (PKA) and glutathione-S-transferase-S6 (GST-S6) for S6K2. Enzyme was pre-incubated with substrate and varying concentrations of inhibitor on ice for 30 minutes. The control sample contained solvent (methanol). ATP was then added to each sample and the cocktail incubated at 30° C. for 15 minutes. Equal amounts of each mixture were fractionated by SDS-PAGE on a 10% acrylamide gel. The gel was fixed in 50% methanol/10% acetic acid, washed with water, and then stained in Pro-Q Stain in the dark for 60 minutes. The gel was then destained, washed, and scanned on a Typhoon Imager (FIG. 5).

The effect of DB2ClPP (di-n-butyl 2-chlorophenyl phosphate) on the activity of trypsin was assayed. Trypsin was incubated with solvent, 10 μM DB2CPP, or 10 μM DIFP (a known inhibitor of trypsin) for 60 minutes at 25° C. to determine any inhibitory effect of DB2CPP on enzymatic activity. Enzyme activity is given as nmoles of BAEE hydrolyzed per minute at 25° C. Data shown are the mean of three replicates ±SEM. (FIG. 3)

Figure 4:
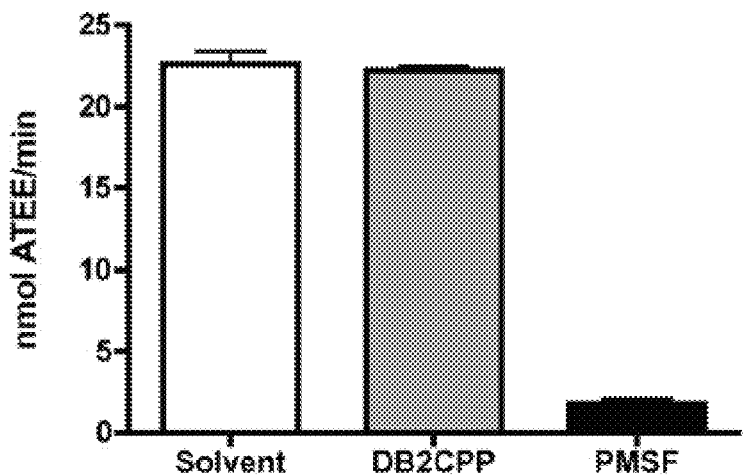
FIG. 4 depicts the effect of DB2ClPP on the activity of chymotrypsin.

The effect of DB2ClPP on the activity of chymotrypsin was assayed. Trypsin was incubated with solvent, 10 μM DB2CPP, or 10 μM PMSF (a known inhibitor of chymotrypsin) for 60 minutes at 25° C. to determine any inhibitory effect of DB2CPP on enzymatic activity. Enzyme activity is given as nmoles of ATEE hydrolyzed per minute at 25° C. Data shown are the mean of three replicates ±SEM. (FIG. 4)

Figure 6:
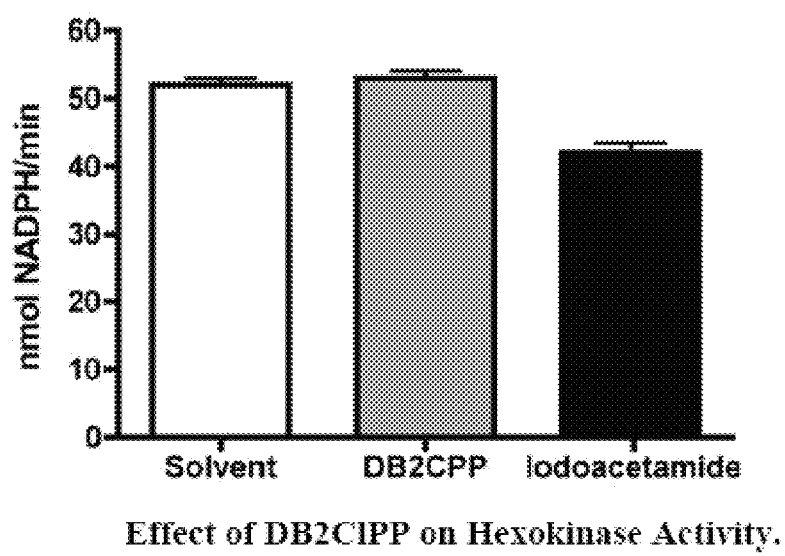
FIG. 6 depicts the effect of DB2ClPP on hexokinase activity.

The effect of DB2ClPP on hexokinase activity was assayed. Hexokinase was incubated with solvent, 10 mM iodoacetamide (a known hexokinase inhibitor), or 10 μM DB2CPP for 60 min at 25° C. Enzyme activity is given as the nmoles of NADPH generated per min at 25° C. Data shown are the mean of three replicates ±SEM. (FIG. 6)

As seen in FIGS. 3 (trypsin), 4 (chymotrypsin), 5 (PKA and S6K2), and 6 (hexokinase), none of the above mentioned enzymes were affected by di-n-butyl 2-chlorophenyl phosphate.

Example 4: Effects of Butyrylcholinesterase Inhibitors on Cells

Figure 7:
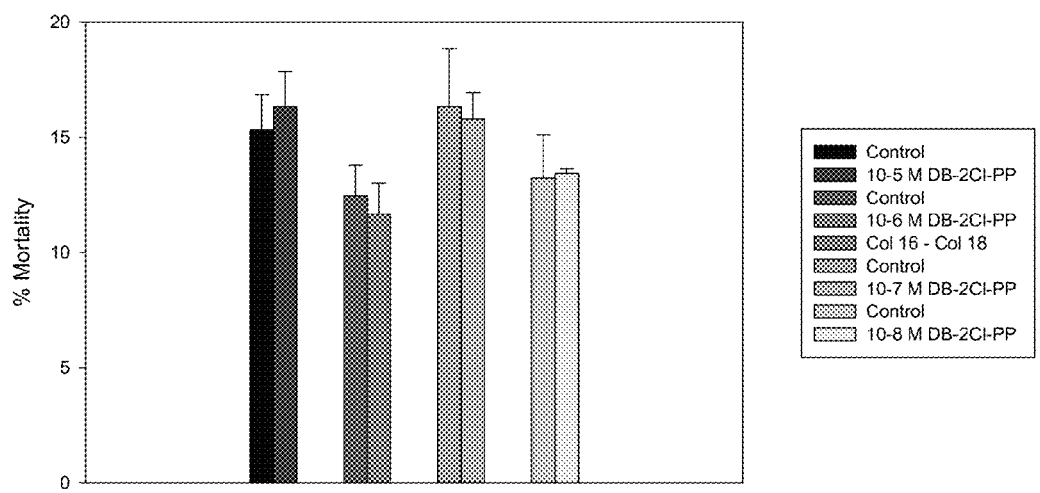
FIG. 7 depicts the lack of toxicity of di-n-butyl 2-chlorophenyl phosphate on porcine umbilical stem cells. Cells were cultured in Neurobasal Medium with increasing concentrations of di-n-butyl 2-chlorophenyl phosphate for 48 hours. Solvent acted as control. Each concentration had its own corresponding control group. Results are expressed as mortality and are the mean of 3 replicates ±SD.
Figure 8:
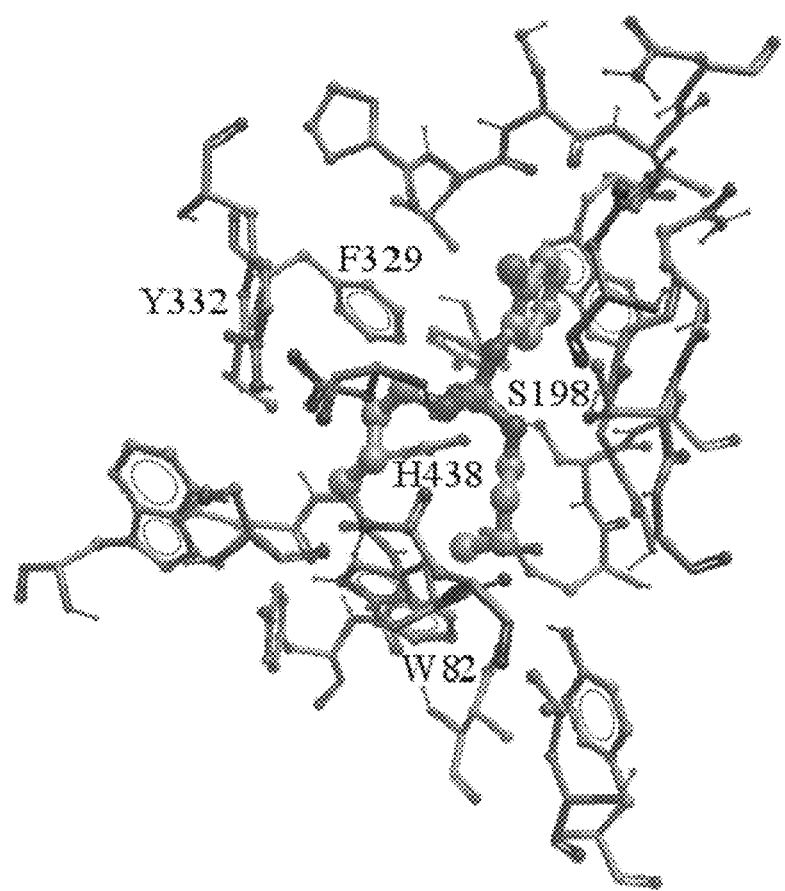
FIG. 8 is a stick rendering which models the flexible docking of a phosphate with AcChase and BuChase.
Figure 9:
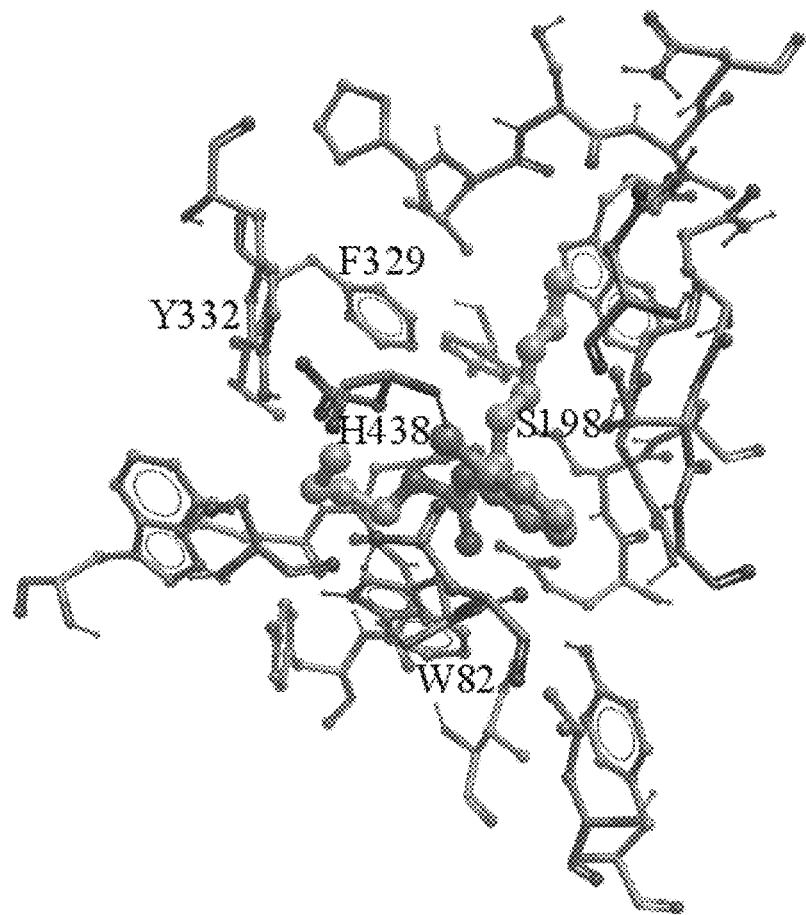
FIG. 9 is a stick rendering which models the flexible docking of a phosphonate with AcChase and BuChase.
Figure 10:
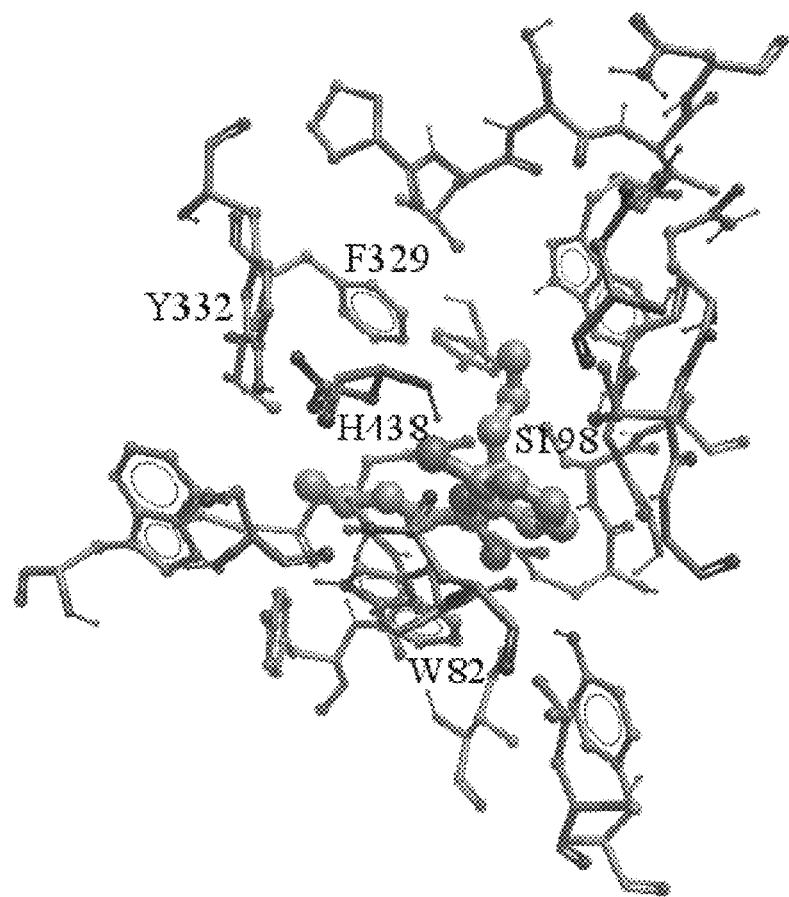
FIG. 10 is a stick rendering modeling the flexible docking of a phosphinate with AcChase and BuChase.
Figure 11:
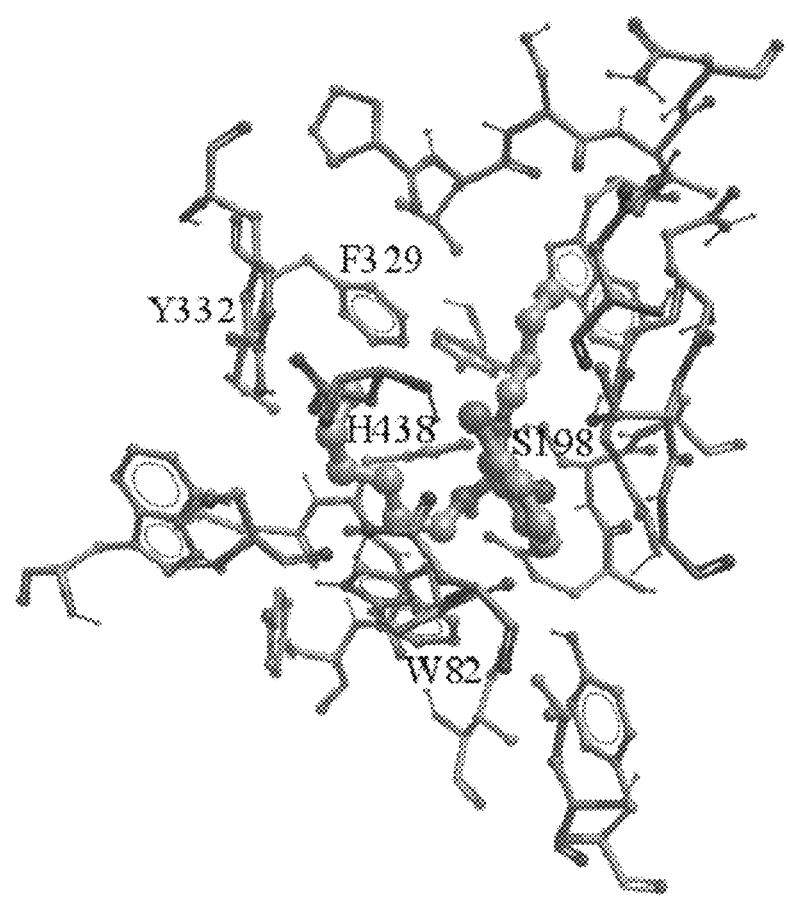
FIG. 11 is a stick rendering modeling the flexible docking of a phosphoramidate with AcChase and BuChase.

Porcine umbilical stem cells were cultured in Neurobasal Medium supplemented with B27 (Invitrogen) and antibiotics for various periods of with varying concentrations of di-n-butyl-2-chlorophenyl phosphate. Cells were collected, washed, counted, and analyzed for viability by Trypan Blue staining. Di-n-butyl-2-chlorophenyl phosphate did not have any significant effect on mortality of the porcine umbilical stem cells (FIG. 7).

In addition, uptake of di-n-butyl-2-chlorophenyl phosphate by porcine umbilical stem cells was measured after 24 and 48 hours of culture (Table 5).

TABLE 5

| Incubation Period | 0 hours | 24 hours | 48 hours |
|---|---|---|---|
| fg DB2Cl-PP/cell (±SEM) | 2.55 ± 0.011 | 11.57 ± 1.02 | 13.62 ± 0.003 |

Also, the uptake of di-n-butyl-2-chlorophenyl phosphate by human umbilical cells was measured after 24 of culture for both undifferentiated cells and differentiating neurons. (Table 6)

TABLE 6

| | 0 hours fg/cell | 24 hours fg/cell |
|---|---|---|
| Undifferentiated | 114.72 ± 37.93 | 795.89 ± 202.41 |
| Neurons | 78.85 ± 8.04 | 820.52 ± 82.32 |

Example 5: Brain Permeability

An animal study using two groups (n=7/group) of male Long-Evans rats (200-225 g, Charles River, Portage, Mich.) was conducted to determine whether DB2ClPP crosses the blood brain barrier. DB2ClPP was dissolved in dimethyl sulfoxide (DMSO). Rats were injected intraperitoneally with either 0.2 mL DMSO (vehicle control) or 0.2 mL of a 10 mg/mL solution of DB2ClPP with DMSO as solvent. Thirty minutes after DB2ClPP treatment, animals were deeply anesthetized with isoflurane and then decapitated. Brains were removed quickly, rinsed in ice cold phosphate buffer saline (pH 7.4) and block dissected and flash frozen in liquid nitrogen and stored at −80° C. until assayed.

The tissue from two animals injected with DB2ClPP were processed as follows: i) brain tissue (1.5 g) was allowed to thaw on ice in a Dounce homogenizer; ii) 10 mL of methylene chloride was added and the tissue extracted with 20 strokes of the loose fitting pestle. The homogenate was clarified by centrifugation and the supernatant extracted three times with methylene chloride using a separatory funnel. The organic phase was collected, pooled, and dried over magnesium sulfate. The eluate was then concentrated down to a volume of approximately 200 μl under nitrogen and analyzed by GC/MS for the presence of the DB2ClPP. A solution of neat DB2ClPP served as control. The DB2ClPP was present in both samples. Based on a standard curve for DB2ClPP, one sample contained 220 ng and the other 125 ng of DB2ClPP.

Example 6: Inhibition of β-Amyloid Peptides

One of the more significant factors affecting patients with Alzheimer's disease is the elevated level of neurotoxic β-amyloid peptide. The most prominent β-amyloid peptides are referred to as Aβ40 and Aβ42 peptides. For our in vitro studies we used neuroblastoma cells as a biological model for evaluating β-amyloid peptide production. Cells were cultured in Eagles MEM containing Glutamax, penicillin and streptomycin, and 0.5% fetal calf serum. To monitor the effects of DB2ClPP, cells were grown for 24 hrs in the presence or absence of $10^{-8}$ M DB2ClPP. The supernatant was collected and concentrated using a 2K centrifugal membrane filter. The concentrated solution was then analyzed by ELISA for Aβ40 and Aβ42 peptides. The results, in pg/mL, are shown below. DB2ClPP at $10^{-5}$ M significantly inhibits formation of the two β-amyloid peptides. Results are expressed as the mean of three assays ±Std. Deviation. One point had only one sample due to a technical error.

TABLE 7

| DB2ClPP | Aβ-40 [pg/mg] | Aβ-42 [pg/mg] |
|---|---|---|
| $10^{-5}$M | 203.1 ± 5.2 | 132.1 ± 2.3 |
| $10^{-6}$M | 111.5 ± 0.5 | 67.4 (one sample) |
| $10^{-8}$M | 87.3 ± 3.4 | 56.9 ± 3.1 |
| No Inhibitor | 122.5 ± 1.7 | 88.5 ± 0.2 |

As demonstrated in the results of Table 7, administration of a higher concentration (i.e., $10^{-5}$ M) of DB2ClPP inhibitor resulted in an increased concentration of Aβ-40 and Aβ-42 peptides as compared to when no inhibitor was administered in the control. However, when a lower concentration of DB2ClPP inhibitor was administered (i.e., $10^{-5}$ M), there was a decreased concentration of Aβ-40 and Aβ-42 peptides, including a lower concentration than when no inhibitor was administered. The decreased concentration of Aβ-40 and Aβ-42 peptides when administering a lower concentration of DB2ClPP is an unexpected result.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A method of reducing a level of a β-amyloid peptide in the brain of a subject in need thereof, comprising administering an effective amount of di-n-butyl 2-chlorophenyl phosphate to the subject such that the di-n-butyl 2-chlorophenyl phosphate has a concentration of about $10^{-6}$ M to about $10^{-8}$ M in the brain of the subject.

2. The method of claim 1, wherein the di-n-butyl 2-chlorophenyl phosphate is administered orally, buccally, transdermally, intranasally, parenterally, intravenously, intramuscularly, subcutaneously, ophthalmically, or rectally.

3. The method of claim 1, wherein a sufficient amount of the compound is administered so that at least about 10 ng of the compound crosses the blood brain barrier of the subject.

4. The method of claim 1, wherein the di-n-butyl 2-chlorophenyl phosphate has a concentration of about $10^{-8}$M in the brain of the subject.

5. The method of claim 1, wherein at least 0.1 mg of the di-n-butyl 2-chlorophenyl phosphate is administered.

6. The method of claim 1, wherein the subject is a human being that is at least about 50 years of age.

7. The method of claim 1, wherein the β-amyloid peptide is Aβ40 or Aβ42.

8. The method of claim 7, wherein the β-amyloid peptide is Aβ40, and the level of Aβ40 in the brain of the subject is reduced by at least about 10%.

9. The method of claim 7, wherein the β-amyloid peptide is Aβ42, and the level of Aβ42 in the brain of the subject is reduced by at least about 10%.

10. The method of claim 1, wherein the subject experiences an elimination, reduction, or prevention of the β-amyloid peptide.

11. The method of claim 1, wherein the subject is suffering from a Alzheimer's disease.

12. A method of treating Alzheimer's disease in a subject in need thereof, comprising administering an effective amount of di-n-butyl 2-chlorophenyl phosphate to the subject such that the di-n-butyl 2-chlorophenyl phosphate has a concentration of about $10^{-6}$M to about $10^{-8}$M in the brain of the subject.

13. The method of claim 12, wherein a β-amyloid peptide concentration in the subject is decreased.

14. The method of claim 12, wherein the β-amyloid peptide is Aβ40 or Aβ42.

15. The method of claim 14, wherein the β-amyloid peptide is Aβ40, and the level of Aβ40 in the brain of the subject is reduced by at least about 10%.

16. The method of claim 14, wherein the β-amyloid peptide is Aβ42, and the level of Aβ42 in the brain of the subject is reduced by at least about 10%.

17. The method of claim 12, wherein the di-n-butyl 2-chlorophenyl phosphate has a concentration of about $10^{-8}$M in the brain of the subject.

18. The method of claim 12, wherein the di-n-butyl 2-chlorophenyl phosphate is administered orally, buccally, transdermally, intranasally, parenterally, intravenously, intramuscularly, subcutaneously, ophthalmically, or rectally.

19. The method of claim 12, wherein the subject experiences an elimination, reduction, or prevention of a β-amyloid peptide.

* * * * *

UNITED STATES PATENT AND TRADEMARK OFFICE
CERTIFICATE OF CORRECTION

PATENT NO. : 9,757,399 B2
APPLICATION NO. : 15/004797
DATED : September 12, 2017
INVENTOR(S) : Roger A. Acey and Kensaku Nakayama It is certified that error appears in the above-identified patent and that said Letters Patent is hereby corrected as shown below:

On the Title Page

In item (73), please replace "JAL THERAPEUTICS, INC." with --JAL THERAPEUTICS, LLC--.

Signed and Sealed this
Twenty-seventh Day of December, 2022

Katherine Kelly Vidal
*Director of the United States Patent and Trademark Office*